US012637405B2

(12) United States Patent
Gorke et al.

(10) Patent No.: US 12,637,405 B2
(45) Date of Patent: *May 26, 2026

(54) INTEGRATED PROCESS FOR GENERATING ACID ANHYDRIDES

(71) Applicant: Cleantech Building Materials PLC, London (GB)

(72) Inventors: Johnathan Gorke, Charlotte, NC (US); Brian Hashiguchi, Naperville, IL (US); Michael Konnick, Aurora, IL (US); Jay Kouba, St. Helena, CA (US); Erik Scher, San Francisco, CA (US); Jeremy Patt, Naperville, IL (US); Mary Bjorklund, Lombard, IL (US)

(73) Assignee: Cleantech Building Materials PLC, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/738,607

(22) Filed: May 6, 2022

(65) Prior Publication Data

US 2022/0371983 A1 Nov. 24, 2022

Related U.S. Application Data

(60) Provisional application No. 63/185,169, filed on May 6, 2021.

(51) Int. Cl.
*C07C 51/56* (2006.01)
*C07C 51/083* (2006.01)
*C07C 51/573* (2006.01)

(52) U.S. Cl.
CPC ............ *C07C 51/56* (2013.01); *C07C 51/083* (2013.01); *C07C 51/573* (2013.01)

(58) Field of Classification Search
None
See application file for complete search history.

(56) References Cited

U.S. PATENT DOCUMENTS 2,163,013 A 6/1939 Schulz
3,111,548 A 11/1963 Altenschöpfer et al.
(Continued)

FOREIGN PATENT DOCUMENTS

CN 102675080 A 9/2012
DE 408715 C 1/1925
(Continued)

OTHER PUBLICATIONS

Cason, "B-Methylglutaric Anhydride," *Org. Synth.*, 38: 52-53 (1958).
(Continued)

*Primary Examiner* — Amy C Bonaparte
(74) *Attorney, Agent, or Firm* — Leydig, Voit & Mayer, Ltd.

(57) ABSTRACT

Provided is a first process of producing an anhydride of an organic mono-acid comprising performing a transanhydridization reaction of an organic mono-acid and a thermally regenerable anhydride to produce the anhydride of the organic mono-acid and an acid of the thermally regenerable anhydride, wherein at least one of the organic mono-acid and thermally regenerable anhydride is provided by a pre-process that is integrated with the first process. An anhydride production system that is integrated with at least one pre-process, a wood acetylation process coupled to an acetic anhydride production process, a process of supplying an acetic acid reactant feed to a transanhydridization reaction unit, and an integrated wood acetylation and anhydride production system also are provided.

10 Claims, 13 Drawing Sheets

(56) References Cited

U.S. PATENT DOCUMENTS

| | | | | |
|---|---|---|---|---|
| 3,513,180 | A | 5/1970 | Fenton et al. | |
| 4,002,677 | A | 1/1977 | Naglieri et al. | |
| 4,234,719 | A | 11/1980 | Wan | |
| 11,608,306 | B2 * | 3/2023 | Gorke | C07C 51/56 |
| 2017/0204043 | A1 * | 7/2017 | Benstead | C07C 51/56 |
| 2021/0347722 | A1 * | 11/2021 | Gorke | C07C 303/22 |

FOREIGN PATENT DOCUMENTS

| | | | |
|---|---|---|---|
| WO | WO 2016/009051 | A1 | 1/2016 |
| WO | WO 2021/226433 | A1 | 11/2021 |
| WO | WO 2022/236127 | A1 | 11/2022 |

OTHER PUBLICATIONS

Besrat et al., "Mammalian Metabolism of Glutaric Acid," *J. Biol. Chem.*, 244(6): 1461-1467 (1969).
Haddadin et al., "Solvolytic Reactions of Cyclic Anhydrides in Anhydrous Acetic Acid," *J. Pharm. Sci.*, 64(11): 1759-1765 (1975).
European Patent Office, International Search Report and Written Opinion in International Patent Application No. PCT/US2022/028175 (Sep. 9, 2022).

* cited by examiner

X and X' = -C(O)-, -S(O)-, -S(O)2-, -P(O)(OH)-, -P(O)(R")-
R, R' and R" = alkyl, heteroalkyl, aryl, heteroaryl

$$H_6P_4O_{13} + H_2O \longrightarrow H_5P_3O_{10} + H_3PO_4 \quad (1)$$

$$H_5P_3O_{10} + H_2O \longrightarrow H_4P_2O_7 + H_3PO_4 \quad (2)$$

$$H_4P_2O_7 + H_2O \longrightarrow 2\ H_3PO_4 \quad (3)$$

or (4)

(5)

acetic anhydride glutaric acid acetic acid glutaric anhydride water

INTEGRATED PROCESS FOR GENERATING ACID ANHYDRIDES

BACKGROUND OF THE INVENTION

Anhydrides are useful, reactive species that have broad application in the chemical, polymer, pharmaceutical, and food and beverage industries. The reactivity of the anhydride group makes them useful, as example as water scavengers, in the preparation of esters and polyesters, as monomers for polymers, and as catalysts. Specific applications include use as an acetylating agent in the preparation of cellulose acetate, acetylated wood materials, tetraacetylethylenediamine bleach activators, and aspirin, as monomers in the production of unsaturated polyesters and high-performance polyimides, and as catalysts in the petroleum and petrochemical industries for dehydration, polymerization, condensation, alkylation, and isomerization processes.

In the production of anhydrides, the direct condensation of acids is an energetically unfavorable reaction, particularly for monoacid species, so the synthesis of these anhydrides typically is energy intensive, carried out at elevated temperatures and pressures, and/or is poorly selective in the product formation.

Acetic anhydride is produced commercially by three routes: ketene reaction, carbonylation of methyl acetate, and direct oxidation of acetaldehyde. The ketene route is the most widely practiced industrial acetic anhydride process and involves pyrolyzing acetic acid or acetone to ketene at reduced pressure and very high temperature, then reacting the ketene with acetic acid at near ambient temperature in a compressor (see, e.g., U.S. Pat. No. 3,111,548). The carbonylation process involves esterification of acetic acid with methanol to form methyl acetate at moderate temperature. The methyl acetate is then reacted with carbon monoxide at elevated temperature and high pressure (see, e.g., U.S. Pat. No. 4,002,677). Water is also added to the reactor to control the ratio of acetic acid and acetic anhydride. While it is conducted at low temperature and pressure, the direct oxidation of acetaldehyde route suffers from low selectivity (about 80 mol % versus greater than 90 mol % for the other routes) making it economically unattractive. Analogous versions of the above routes are known for producing other anhydrides, although one common technique is to use excess acetic anhydride to produce other desired anhydrides.

Production of acetic anhydride from reacting acetic acid with a cyclic anhydride, such as glutaric anhydride, has been described in the literature (Haddadin et al., *J. Pharm. Sci.,* 1975, 64(11), 1759-1765). However, these experiments rely on having a large excess of acetic acid present as well as a strong acid catalyst (e.g., perchloric acid) to achieve <10% acetic anhydride (relative to acetic acid). As this equilibrium lies heavily on the side of glutaric anhydride, one efficient and practiced industrial method for glutaric anhydride production involves treatment of glutaric acid and its derivatives with a slight excess of acetic anhydride to generate glutaric anhydride quantitatively (Cason, *Org. Synth.,* 1958, 38, 52; and Besrat et al., *J. Biol. Chem.,* 1969, 244(6), 1461-1467). In practice however, this reaction is presumed to be practically irreversible, no processes have described utilization of this reverse reaction to generate acetic anhydride, and no methods utilizing low acetic acid/glutaric anhydride ratios have been described to date. Furthermore, the coupling of this type of non-thermally generable anhydride production reaction with a thermally regenerable anhydride reaction (e.g., glutaric acid to glutaric anhydride and water) to create a continuous process has not been described.

Not all processes to produce anhydrides are readily commercially scalable. A complex process that requires the use of specialized equipment and metallurgy will have a high capital cost per pound of product. At low production volumes, the capital costs become even a larger contributor to production cost.

Thus, there remains a need for alternative syntheses for producing anhydrides that work under less harsh conditions while still maintaining a high degree of selectivity and that can be integrated with other anhydride-related processes.

BRIEF SUMMARY OF THE INVENTION

The invention provides a method of producing an anhydride of an organic mono-acid comprising contacting an organic mono-acid and a thermally regenerable anhydride to produce the anhydride of the organic mono-acid and either a diacid of the regenerable anhydride, a partially hydrolyzed regenerable anhydride, or both a diacid of the regenerable anhydride and a partially hydrolyzed regenerable anhydride.

The invention also provides a first process of producing an anhydride of an organic mono-acid comprising performing a transanhydridization reaction of an organic mono-acid and a thermally regenerable anhydride to produce the anhydride of the organic mono-acid and an acid of the thermally regenerable anhydride, wherein at least one of the organic mono-acid and thermally regenerable anhydride is provided by a preprocess that is integrated with the first process.

The invention further provides an anhydride production system that is integrated with at least one anhydride-related preprocess, a wood acetylation process coupled to an acetic anhydride production process, a process of supplying an acetic acid reactant feed to a transanhydridization reaction unit, and an integrated wood acetylation and anhydride production system.

BRIEF DESCRIPTION OF THE SEVERAL VIEWS OF THE DRAWINGS

FIG. 4A is a schematic showing wood acetylation process of the prior art. FIG. 4B is a schematic showing a wood acetylation vessel for receiving wood and an acetylation fluid that is in fluid communication with a first fluid channel for conveying recovered acetylation fluid; separation vessel #1 for receiving the recovered acetylation fluid from the first fluid channel and that is in fluid communication with a recovered acetic anhydride vessel and an acetic acid by-product vessel; a transanhydridization ("TRANS") vessel for receiving acetic acid by-product and a thermally regenerable anhydride (TRA) that is in fluid communication with (a) the acetic acid by-product vessel; and (b) a second fluid channel for conveying the thermally regenerable anhydride; a third fluid channel for conveying acetic anhydride and an acid of the thermally regenerable anhydride to separation vessel #2; a fourth fluid channel for conveying separated acetic anhydride from separation vessel #2 to anhydride vessel #1; a fifth fluid channel for conveying separated acid of the thermally regenerated anhydride from separation vessel #2 to a regeneration vessel. Anhydride vessel #1 is in fluid communication with the wood acetylation vessel; and the regeneration vessel is in fluid communication with the second fluid channel.

DETAILED DESCRIPTION OF THE INVENTION

The invention provides an anhydride production process that occurs at ambient or near-ambient pressure and moderate temperatures (e.g., about 240° C. or lower). Moreover, the process does not require a catalyst to generate anhydride at high selectivity. The process can use relatively inexpensive dehydrating agents, including industrial byproducts (e.g., glutaric anhydride) and/or low-cost materials (e.g., polyphosphoric acid). The process does not use or generate hazardous reactants, intermediates, or by-products (e.g., ketene, carbon monoxide, halogenated by-products, or thermal or chemical oxidizers) and does not require expensive noble metals or environmentally damaging phosphate catalysts. As an added advantage, the inventive process does not require adding a third component (e.g., water) to the system to control the acid/anhydride ratio as needed in the standard carbonylation process. Rather, the residence time and/or relative flow rates of the starting acid and regenerable anhydride can be manipulated to adjust the ratio.

The anhydride production process and equipment for the reaction and recovery are relatively simple and readily scalable, as compared to currently deployed commercial process technologies to produce acid anhydrides. For example, the anhydride production process does not require cracking furnaces, as used in ketene plants. Thus, the simplicity and scalability of the anhydride production process provide an economic route to produce commercial grade acid anhydrides. The term "scalable," as used herein, refers to a process that can be economic (relative to products produced) at low production values, e.g., about 5-50 kmta range (i.e., scaled down) and at large production values (again, relative to products produced), e.g., >50-100 kmta levels. In some aspects, the process is used on a small scale (e.g., 5-20 kmta) a medium scale (e.g., 20-50 kmta), a large scale (e.g., 50-300 kmta, 50-100 kmta, 100-300 kmta, or 100-200 kmta). In addition, commercial processes that utilize acid anhydrides typically yield a low value acid by-product stream. Accordingly, the anhydride production process can be collocated and integrated into commercial processes to convert these low value acid streams to high value product acid anhydrides. In certain embodiments, the low value acid streams can be taken from downstream anhydride-consuming processes without additional purification. In certain other embodiments, the anhydride produced can contain by-products, which do not negatively impact an integrated anhydride-consuming process.

Figure 1:
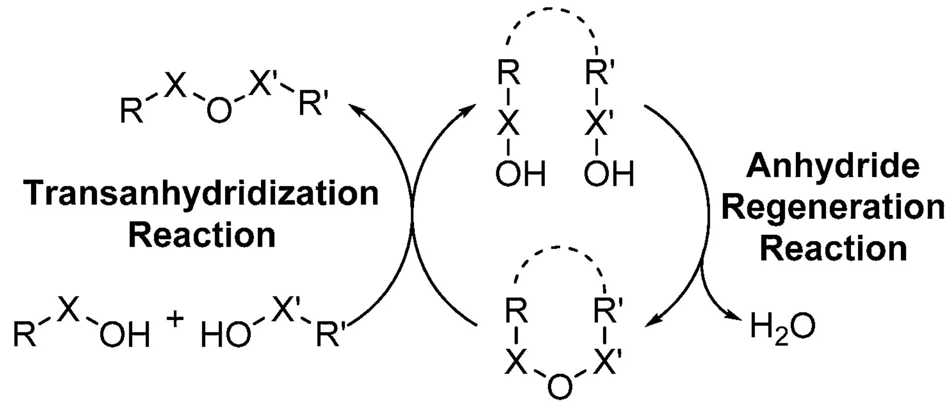
FIG. 1 contains two different generalized schemes illustrating the two-step process of: 1) conversion of an organic mono-acid and a regenerable anhydride to the anhydride or mixed anhydride of the organic mono-acid and the hydrolyzed regenerable anhydride (transanhydridization reaction) and 2) the regeneration of the regenerable anhydride with loss of water (anhydride regeneration reaction).
Figure 1:
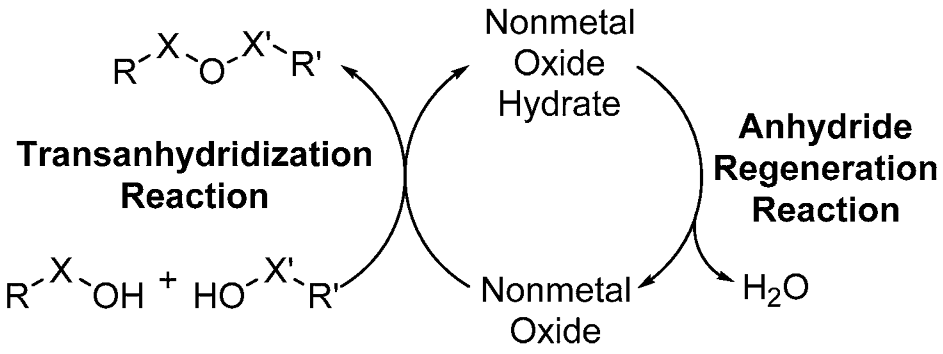
Figure 2:
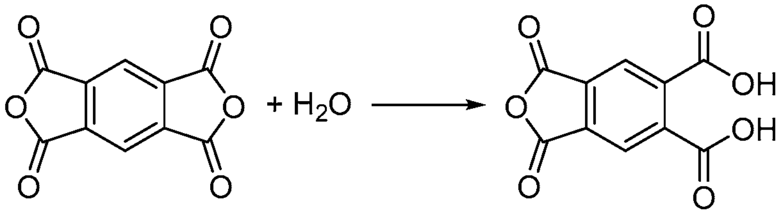
FIG. 2 is a series of reactions showing hydrolysis of an anhydride to form a partially hydrolyzed anhydride using, for example, polyphosphoric acid and pyromellitic anhydride.
Figure 2:
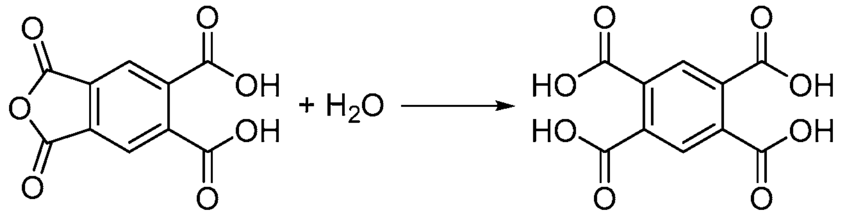

In particular, the invention provides a method of producing an anhydride of an organic mono-acid comprising contacting an organic mono-acid and a thermally regenerable anhydride to produce the anhydride of the organic mono-acid and either a diacid of the thermally regenerable anhydride, a partially hydrolyzed anhydride, or both a diacid of the anhydride and a partially hydrolyzed anhydride. This transanhydridization reaction is illustrated in FIG. 1. Generation of a partially hydrolyzed anhydride is shown in FIG. 2. In general, a stream containing at least one organic mono-acid ("organic mono-acid" or "organic acid") is reacted with a stream containing at least one anhydride that is capable of being regenerated ("thermally regenerable anhydride" or "regenerable anhydride"). The reaction yields a stream containing one or more desired anhydrides and the acid form(s) of the regenerable anhydride(s), as well as unreacted acid and unreacted, regenerable anhydride. The reaction can be run to completion or to partial completion at various ratios of the reactants.

Following the reaction, the residual reactants and products are separated into various streams in one or more steps. For example, the method comprises a separation step comprising forming a first stream comprising the anhydride of the organic mono-acid (desired product) and any unreacted organic mono-acid and forming a second stream comprising the diacid of the regenerable anhydride, partially hydrolyzed anhydride, and/or unreacted anhydride. In some embodiments, residual unreacted regenerable anhydride is extracted from its acid form to drive the regeneration reaction forward. Alternatively or in addition, in some embodiments, the first stream comprising the anhydride of the organic mono-acid (desired product) and any unreacted organic mono-acid are recycled back to an integrated preprocess, as described herein. If desired, the first stream can undergo additional processing, such as drying.

The separation steps described herein can use any suitable method of physical separation, including distillation (e.g., simple, molecular, evaporative, short path, batch, continuous, flash, steam, vacuum, low temperature, fractional, azeotropic, extractive, or a combination thereof). In some embodiments and depending on the reactants, the separation step is by either fractional distillation, azeotropic distillation, and/or extractive distillation. In some embodiments, the transanhydridization reaction products are sent to a flash vessel that separates the mixture into flash vapor and flash liquid. The flash vapor can be further subjected to separation (e.g., distillation), and the flash liquid can be sent to a vessel that strips out unreacted organic mono-acid (e.g., acetic acid) and the produced anhydride to leave a mixture that includes unreacted starting anhydride and waste compounds.

In an azeotropic distillation or other distillation with two or more compounds with a close boiling point differential, typically a new component (e.g., entrainer) is added to the azeotrope or otherwise inseparable mixture. The new component serves to form two or more immiscible liquid phases that can be separated. In addition, a third component such as a solid dehydrating agent can be added, e.g., molecular sieves, silica gel, alumina, other thermally regenerable solid drying agents, and combinations thereof.

Azeotropic distillation can be performed as homogenous azeotropic distillation, heterogeneous azeotropic distillation, reactive distillation, and salted distillation. In homogenous azeotropic distillation, an entrainer is added that is miscible with the original mixture. In heterogeneous azeotropic distillation, an entrainer is added that forms a heterogeneous azeotrope with one or more components in the original mixture. In reactive distillation, an entrainer is added that reacts with one or more components in the original mixture. The non-reacting component is produced as a distillate, and the entrainer is recovered from the reverse reaction. Salted distillation is a type of extractive distillation, in which relative volatility is altered by the addition of salt as an entrainer.

In certain embodiments, the unreacted organic mono-acid is separated from the anhydride of the organic mono-acid. If desired, the separated, unreacted organic mono-acid can be recycled for reuse as a starting material. In some instances, a portion of the unreacted organic mono-acid is diverted to a vessel containing the second stream. In such instances, it is believed that the recycled organic mono-acid can act as an entrainer or azeotroping agent to remove water during regeneration of the regenerable anhydride.

The regenerable anhydride is regenerated by removing water from the multi-acid form of the regenerable anhydride. In any of the foregoing embodiments, to regenerate the anhydride the second stream can be optionally heated in the presence or absence of a catalyst and subjected to distillation (e.g., azeotropic distillation). Preferably, the regenerable anhydride is regenerated in a separate step from the reaction that generates the anhydride of the organic mono-acid. If desired, the regenerated anhydride can be recycled for reuse as a starting material.

The reactants and products of the inventive method can be separated and/or concentrated by a number of different unit operations. The reaction and separation steps can be combined or coupled. Similarly, the separation and regeneration steps can be combined or coupled. Unit operations include, for example, reaction, regeneration, distillation, extractive distillation, reactive distillation, extraction, reactive extraction, mixing-settling, pervaporation, membrane separation, evaporation, condensation, flashing, fractionation, electrotreatment, flotation, phase separation, coalescence, hydrocycloning, decanting, parametric pumping, sublimation, ion exchange, adsorption, absorption, and/or crystallization.

In the method, the anhydride starting material is any suitable regenerable anhydride. In some instances, the regenerable anhydride is cyclic or can form a cyclic structure. It has been observed that an anhydride with a cyclic structure or that can form a cyclic structure can be more easily thermally regenerated. In some embodiments, the thermally regenerable anhydride is selected from a carboxylic acid anhydride, a sulfonic acid anhydride, a phosphinic acid anhydride, a phosphonic acid anhydride, a phosphoric acid anhydride, and a mixed anhydride. In some embodiments, the mixed anhydride contains a combination of different acid moieties. In some embodiments, the mixed anhydride has different backbone structures (e.g., a mixed anhydride created from the condensation of the organic mono-acid in the feed and another acidic moiety). Preferably, at least a portion of the structure of the mixed anhydride is in cyclic form or capable of forming a cyclic structure.

In general, the regenerable carboxylic acid anhydride has a cyclic structure of the formula $R^1$—C(O)—O—C(O)—$R^2$, in which $R^1$ and $R^2$ are linked together to form an alkylene with 1 or 2 optional double bonds, arylene, or a mixed alkylene/arylene group. The mixed alkylene/arylene group can in some instances form dianhydride or trianhydride. The alkylene with 1 or 2 optional double bonds, arylene, and mixed alkylene/arylene group is optionally substituted with one or more substituents (e.g., 1, 2, 3, 4, 5, 6, etc.) selected from alkyl (including alkylene), halo, alkoxy, trialkylsiloxy, nitro, aryl, and carboxy-substituted phenyl. Examples of the carboxylic acid anhydride include, e.g., tetrafluorosuccinic anhydride, maleic anhydride, itaconic anhydride, succinic anhydride, glutaric anhydride, 2,7-oxepanedione (adipic anhydride), azelaic anhydride, suberic anhydride, sebacic anhydride, 3-methylglutaric anhydride, methylsuccinic anhydride, 3-(t-butyldimethylsilyloxy)glutaric anhydride, 1,2-cyclohexanedicarboxylic anhydride, 1,3-cyclohexanedicarboxylic anhydride, camphoric anhydride, homophthalic anhydride, phthalic anhydride, isophthalic anhydride, trimellitic anhydride, pyromellitic dianhydride, mellitic trianhydride, and 3- or 4-fluorophthalic anhydride.

In general, a regenerable sulfonic acid anhydride has the formula $R^3—S(O)_2—O—S(O)_2—R^4$, in which $R^3$ and $R^4$ are the same or different and each is a $C_1$-12 alkyl group or aryl group (e.g., phenyl) or $R^3$ and $R^4$ are linked together to form an alkylene, arylene, or mixed alkylene/arylene group. Each $C_{1-12}$ alkyl, aryl, alkylene, arylene, and mixed alkylene/arylene group is optionally substituted with one or more substituents (e.g., 1, 2, 3, 4, or 5) selected from alkyl, halo, alkoxy, trialkylsiloxy, nitro, and aryl. Examples of the sulfonic acid anhydride include, e.g., methanesulfonic anhydride, 1,2-ethane disulfonic anhydride, nonafluorobutanesulfonic anhydride, and p-toluenesulfonic anhydride.

A regenerable phosphinic acid anhydride has the formula $R^5—P(O)(R^6)—O—P(O)(R^7)—R^8$ in which $R^5$, $R^6$, $R^7$, and $R^8$ are the same or different and each is H, a $C_{1-12}$ alkyl group, or aryl group (e.g., phenyl) or $R^5$ and $R^8$ are linked together to form an alkylene, arylene, or mixed alkylene/arylene group. Each $C_{1-12}$ alkyl, aryl, alkylene, arylene, and mixed alkylene/arylene group is optionally substituted with one or more substituents (e.g., 1, 2, 3, 4, or 5) selected from alkyl, halo, alkoxy, trialkylsiloxy, nitro, and aryl. Examples of the phosphinic acid anhydride include, e.g., propane-1,3-bis(methylphosphinic acid) anhydride, butane-1,4-bis(methylphosphinic acid) anhydride, hexane-1,6-bis(methylphosphinic acid) anhydride and decane-(1,10-bismethylphosphinic acid) anhydride.

A regenerable phosphonic acid anhydride has the formula $R^9—P(O)(OH)—O—P(O)(OH)—R^{10}$, $R^9—P(O)(OH)—[O—P(O)(R^{10})]_n—O—P(O)(OH)—R^{11}$, or

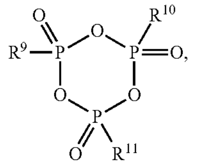

in which $R^9$, $R^{10}$, and $R^{11}$ are the same or different and each is a $C_{1-12}$ alkyl group or aryl group (e.g., phenyl) or $R^9$ and $R^{10}$ are linked together to form an alkylene, arylene, or mixed alkylene/arylene group. Each $C_{1-12}$ alkyl, aryl, alkylene, arylene, and mixed alkylene/arylene group is optionally substituted with one or more substituents (e.g., 1, 2, 3, 4, or 5) selected from alkyl, halo, alkoxy, trialkylsiloxy, nitro, and aryl. Examples of the phosphonic acid anhydride include, e.g., propane-phosphonic acid anhydride, butane-phosphonic acid anhydride, hexane-phosphonic acid anhydride, octane-phosphonic acid anhydride, decane-phosphonic acid anhydride, methane-pyrophosphonic acid anhydride, and propane-pyrophosphonic acid anhydride.

A regenerable phosphoric acid anhydride includes, for example, phosphorus pentoxide, pyrophosphoric acid, trimetaphosphoric acid, polyphosphates, cyclic polyphosphosphates, and polyphosphoric acid.

In some embodiments, the regenerable anhydride forms a polymeric structure. Typically, polymeric structures form with alkyene chains longer than 5 carbons (e.g., C6, C7, C8, C9, C10, etc.). It is believed that a polymeric structure forms when the terminus of one molecule bonds to the terminus of a second molecule and so on. A diacid that forms a polyanhydride can be of the formula $HO_2C—(CH_2)_m—C(O)—O—C(O)—(CH_2)_n—CO_2H$, in which m and n are the same or different and each is an integer from 6 to 12 (i.e., 6, 7, 8, 9, 10, 11, or 12). In some embodiments, the polyanhydride can be of the formula:

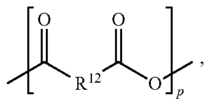

in which $R^{12}$ is $C_{6-12}$ alkylene that optionally contains one or more double bonds, arylene, or a mixture thereof. The alkylene and arylene can be substituted as described herein. The subscript "p" is the number of repeat units and is an integer of at least 2 (e.g., 5 or more, 10 or more, 15 or more, etc.). Examples of the diacid anhydride that can form a polyanhydride include, e.g., adipic anhydride, azelaic anhydride, suberic anhydride, sebacic anhydride, decane anhydride, dodecanedioic anhydride, 1,6-bis(p-carboxyphenoxy)hexane anhydride, 1,3-bis(p-carboxyphenoxy)propane anhydride, p-carboxyphenoxymethane anhydride, p-carboxyphenoxypropane anhydride, p-carboxyphenoxyvaleric anhydride, p-carboxyphenoxyacetic anhydride, p-carboxyphenoxy octanoic anhydride, phenylenedipropionic anhydride, and combinations thereof. The polymeric anhydride can also be mixed in that two different acids are condensed, such as sebacid acid copolymerized with 1,3-bis(p-carboxyphenoxy)propane or 1,6-bis(p-carboxyphenoxy)hexane.

In certain instances, the regenerable anhydride is a mixture of anhydrides that are in cyclic form, capable of forming a cyclic structure, and/or polymeric form.

The regenerable anhydride can also be a mixed anhydride, which includes different organic groups of a single type of anhydride (e.g., benzoic acid-trifluoroacetic acid anhydride) and an anhydride of both a carboxylic acid and a sulfonic acid (e.g., sulfobenzoic anhydride (ortho, meta, and/or para), in particular ortho-sulfobenzoic anhydride), a carboxylic acid and a phosphoric acid, or a sulfonic acid and a phosphoric acid. In some instances, a mixed anhydride is created from the condensation of the organic mono-acid and another acidic moiety present in the reaction.

In preferred embodiments, the regenerable anhydride is succinic anhydride, glutaric anhydride, nitrophthalic anhydride, homophthalic anhydride, 1,2-ethane disulfonic acid, polyphosphoric acid, pyromellitic anhydride, propanephosphonic anhydride, ortho-sulfobenzoic anhydride, mixed benzoic acid-trifluoroacetic acid anhydride, polyphosphoric anhydride, or any combination thereof. More preferably, the anhydride is glutaric anhydride.

The regenerable anhydride can be added to the reaction in any suitable manner.

The organic mono-acid is a carboxylic acid, a sulfonic acid, a sulfinic acid, a phosphonic acid, or a phosphinic acid. In general, the carboxylic acid is of the formula R—C(O)OH; the sulfonic acid is of the formula R—S(O)$_2$OH; the sulfinic acid is of the formula R—S(O)OH; the phosphonic acid is of the formula R—P(O)(OH)$_2$; and the phosphinic acid is of the formula R—P(R')(O)OH. In any of the foregoing formulas, R is $C_{1-18}$ alkyl or aryl. R' is H, $C_{1-18}$ alkyl, or aryl. The $C_{1-18}$ alkyl and aryl groups for R and R' can be optionally substituted with one or more substituents (e.g., 1, 2, 3, 4, 5, 6, etc.) selected from alkyl, halo, alkoxy, trialkylsiloxy, nitro, and aryl.

In some instances, the organic mono-acid is a $C_{1-18}$ monocarboxylic acid, halo-substituted $C_{1-18}$ monocarboxylic acid (e.g., chloroacetic acid or trifluoroacetic acid), an aryl-containing acid (e.g., benzoic acid or cinnamic acid), methanesulfonic acid, or In some instances, the organic mono-acid is a $C_{1-18}$ monocarboxylic acid such as, e.g., formic acid, acetic acid, propionic acid, butanoic acid (butyric acid), isobutyric acid, pentanoic acid (valeric acid), hexanoic acid (caproic acid), heptanoic acid, octanoic acid (caprylic acid), nonanoic acid (pelargonic acid), decanoic acid (capric acid), undecanoic acid (undecylic acid), dodecanoic acid (lauric acid), tridecanoic acid (tridecylic acid), tetradecanoic acid (myristic acid), pentadecanoic acid (pentadecylic acid), hexadecanoic acid (palmitic acid), heptadecanoic acid (margaric acid), octadecanoic acid (stearic acid), or a combination thereof. In a preferred embodiment, the organic mono-acid is acetic acid.

If desired, the organic mono-acid can be added in the form of a salt. While not wishing to be bound by any theory, it is believed that a salt facilitates generation of non-volatile mixed anhydride intermediates that are more kinetically favorable for forming the desired anhydride product from the organic mono-acid (e.g., monocarboxylic acid) than the anhydride (e.g., cyclic anhydride) alone. The organic mono-acid can be, for example, a salt of an alkali metal (e.g., Group 1 cations, such as lithium, sodium, or potassium), an alkaline earth metal (e.g., Group 2 cations, such as calcium, magnesium, and barium), a transition metal (e.g., Group 3-12 cations, such as Fe(II), Zn(II), Cu(I), Cu(II), Cr(II), Al(III), Mn(II), or Ni(II)), or ammonium. In any of the foregoing formulas of the organic mono-acid, one or more hydrogens can be replaced with a cation ($X^+$), such as R—C(O)—$O^-X^+$. Examples of a salt of an organic mono-acid include, e.g., lithium acetate and potassium isobutyrate.

The organic mono-acid can be present in the reactor and/or added to the reaction in a single stage or over multiple stages (e.g., 2 or more stages, 3 or more stages, 4 or more stages, 5 or more stages, 6 or more, etc.). Additionally, the organic mono-acid can be added in an amount that is sub-stoichiometric to, stoichiometric to, or in excess of the regenerable anhydride. In certain embodiments, the organic mono-acid is present in the reactor in an amount that is in excess of the regenerable anhydride. In such scenarios, the ratio of organic mono-acid to regenerable anhydride ranges from 1:1 to 10:1 or is 1:1 or more (e.g., 2:1 or more, 3:1 or more, 4:1 or more, 5:1 or more, 6:1 or more, 7:1 or more, 8:1 or more, or 9:1 or more) and/or 10:1 or less (e.g., 9:1 or less, 8:1 or less, 7:1 or less, 6:1 or less, 5:1 or less, 4:1 or less, 3:1 or less, or 2:1 or less). Any two of the foregoing endpoints can be used to define a close-ended range, or a single endpoint can be used to define an open-ended range.

In any of the embodiments above, the term "alkyl" implies a straight-chain or branched alkyl substituent containing from, for example, from about 1 to about 18 carbon atoms, e.g., from about 1 to about 14 carbon atoms, from about 1 to about 12 carbon atoms, from about 1 to about 10 carbon atoms, from about 1 to about 8 carbon atoms, from about 1 to about 6 carbon atoms, or from about 1 to about 4 carbon atoms. Examples of alkyl group include methyl, ethyl, n-propyl, isopropyl, n-butyl, sec-butyl, isobutyl, tert-butyl, n-pentyl, isopentyl, n-hexyl, n-heptyl, n-octyl, n-nonyl, n-decyl, n-dodecyl, and the like. The alkyl can be substituted or unsubstituted, as described herein.

The term "alkylene" refers to a divalent alkyl group, such as methylenyl (—$CH_2$—), ethylene (—$CH_2CH_2$—), propylene (—$CH_2CH_2CH_2$—), etc., in which the alkyl group is as described above. The alkylene can optionally include 1 or 2 double bonds, such as (—CH═CH—), (—CH═$CHCH_2$—), or (—$CH_2$CH═CH—). Preferably, the alkylene contains from about 1 to about 6 carbon atoms, from about 1 to about 4 carbon atoms, or from about 1 to about 3 carbon atoms. The alkylene can be substituted as described herein.

In any of the embodiments above, the term "aryl" refers to a mono, bi, or tricyclic carbocyclic ring system having one, two, or three aromatic rings, for example, phenyl, naphthyl, anthracenyl, or biphenyl. The term "aryl" refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. Preferably, the aryl is phenyl. An aryl moiety generally contains from, for example, 6 to 30 carbon atoms, from 6 to 18 carbon atoms, from 6 to 14 carbon atoms, or from 6 to 10 carbon atoms. It is understood that the term aryl includes carbocyclic moieties that are planar and comprise $4n+2$ $\pi$ electrons, according to Hückel's Rule, wherein n=1, 2, or 3. The aryl can be substituted or unsubstituted, as described herein.

The term "arylene" refers to a divalent aryl group, such as divalent phenylene, etc., in which the aryl group is as described above. The arylene can be substituted as described herein.

In any of the embodiments above, the term "halo" refers to a halogen moiety selected from fluoro, chloro, bromo, and iodo.

In any of the embodiments above, the term "alkoxy" embrace a linear or branched alkyl group that is attached to a divalent oxygen. The alkyl group is the same as described herein.

In any of the foregoing embodiments, the method can further comprise a suitable solvent. One purpose of a solvent may be to increase the rate of anhydride generation of the reaction by manipulating the dielectric constant and/or solvation properties of the mixture. Without wishing to be bound by theory, it is believed that running the reaction in a high dielectric solvent, such as sulfolane or dimethylsulfoxide (DMSO), could allow for more efficient reactions with organic mono-acids, such as polyphosphoric acid and low dielectric carboxylic acids. Another purpose of the solvent may be to act as an entrainer or azeotroping agent to facilitate the separation of compounds in the system, particularly the product from the starting material. A temperature- or pressure-swing distillation system can be used to facilitate further separation of either bottoms, distillate, or both. The solvent can be, for example, protic or aprotic and preferably has a dielectric constant (F) is that is 15 or more (e.g., F is 20 or more, 25 or more, 30 or more, 35 or more, 40 or more, etc.). The higher the dielectric constant, the higher the polarity of the solvent. Examples of suitable solvents include acetone, acetonitrile, N,N-dimethylacetamide, N,N-dimethylformamide (DMF), formamide, hexamethylphosphoramide, dimethylsulfoxide (DMSO), sulfolane, methanol, ethanol, ispropanol, nitrobenzene, nitromethane, cyclohexanone, methyl ethyl ketone, methyl cyclohexane, toluene, m-xylene, o-xylene, p-xylene, and any combination thereof. A preferred solvent comprises DMSO, sulfolane, or a combination thereof. In some embodiments, a solvent is not used.

While typically not necessary, one or more catalysts can be used. In some embodiments of the inventive method, a catalyst can be used to facilitate the regeneration of the anhydride (e.g., cyclic anhydride), increase the rate of product generation, or both. A suitable catalyst can be homogeneous, insoluble but mobile (e.g., a slurry), or heterogeneous. Examples of catalysts include perchloric acid, magnesium chloride, an ion exchange resin (e.g., a macro reticular (macroporous) polystyrene based ion exchange resin with strongly acidic sulfonic groups, such as AMBERLYST™), a perfluorinated resin (e.g., a sulfonated tetrafluoroethylene-based fluoropolymer-copolymer, such as NAFION™), and a combination thereof.

The transanhydridization reaction (FIG. 2) can be run at any suitable temperature. In general, the transanhydridization reaction temperature is moderate, such as 240° C. or below, including 230° C. or below, 220° C. or below, 210° C. or below, 200° C. or below, 180° C. or below, 160° C. or below, 150° C. or below, 145° C. or below, 140° C. or below, 135° C. or below, 130° C. or below, 125° C. or below, 120° C. or below, 115° C. or below, 110° C. or below, 105° C. or below, 100° C. or below, 95° C. or below, 90° C. or below, 85° C. or below, 80° C. or below, 75° C. or below, 70° C. or below, 65° C. or below, 60° C. or below, 55° C. or below, or 50° C. or below. Typically, the transanhydridization reaction temperature is performed at 45° C. or more (e.g., 50° C. or more, 60° C. or more, 70° C. or more, 80° C. or more, 90° C. or more, 100° C. or more, 110° C. or more, 120° C. or more, 130° C. or more, or 140° C. or more). Any two of the foregoing endpoints can be used to define a close-ended range, or a single endpoint can be used to define an open-ended range. In some preferred embodiments, the reaction temperature is about 150° C. or below, more preferably 120° C. or below, 115° C. or below, or 80° C. or below.

The transanhydridization reaction can be run under any suitable pressure and typically is run at ambient pressure (e.g., atmospheric pressure at 1 atm (101 kPa)) or near-ambient pressure (e.g., 1 atm (101 kPa)±10%, 1 atm (101 kPa)±5%, 1 atm (101 kPa)±2%, or 1 atm (101 kPa)±1%). In some embodiments, the transanhydridization reaction is run under pressure, such as 15 atm (1520 kPa) or less (e.g., 10 atm (1013 kPa) or less, 8 atm (810 kPa) or less, 6 atm (608 kPa) or less, 5 atm (507 kPa) or less, 4 atm (405 kPa) or less, 3 atm (304 kPa) or less, or 2 atm (203 kPa) or less). In such embodiments, the reaction pressure typically will be at 1 atm or more (e.g., 2 atm (203 kPa) or more, 3 atm (304 kPa) or more, 4 atm (405 kPa) or more, 5 atm (507 kPa) or more, 6 atm (608 kPa) or more, 7 atm (709 kPa) or more, 8 atm (810 kPa) or more, 9 atm (912 kPa) or more, 10 atm (1013 kPa) or more, or 12 atm (1216 kPa) or more). For the separation step (e.g., the pressure in a stripping column), the pressure typically is lower to help prevent the reverse reaction from proceeding, such as 0.01 atm (1 kPa) or more (e.g., 0.02 atm (2 kPa) or more, 0.05 atm (5 kPa) or more, 0.07 (7 kPa) atm or more, 0.1 atm (10 kPa) or more, 0.2 atm (20 kPa) or more, 0.5 atm (51 kPa) or more, 0.8 atm (81 kPa) or more, 1 atm (101 kPa) or more and/or 5 atm (507 kPa) or less, 2 atm (203 kPa) or less, 1 atm (101 kPa) or less, 0.8 atm (81 kPa) or less, 0.5 atm (507 kPa) or less, 0.2 atm (20 kPa) or less, or 0.1 atm (10 kPa) or less). Any two of the foregoing endpoints can be used to define a close-ended range, or a single endpoint can be used to define an open-ended range.

The transanhydridization reaction be can run for any suitable length of time. The reaction time can be on the order of minutes or hours (e.g., 5 min or more, 10 min or more, 15 min or more, 30 min or more, 45 min or more, 1 hour or more, 1.5 hours or more, 2 hours or more, 3 hours or more, 4 hours or more, or 5 hours or more). Typically the reaction run will be complete in 4 days or less (e.g., 3.5 days or less, 3 days or less, 2.5 days or less, 2 days or less, 1 day or less, 20 hours or less, 15 hours or less, 10 hours or less, 8 hours or less, 6 hours or less, 5 hours or less, 4 hours or less, 3 hours or less, 2 hours or less, or 1 hour or less). Any two of the foregoing endpoints can be used to define a close-ended range, or a single endpoint can be used to define an open-ended range.

The anhydride regeneration reaction (FIG. 2) can be run at any suitable temperature that regenerates the anhydride (e.g., 350° C. or below, 325° C. or below, 300° C. or below, 275° C. or below, 250° C. or below, 225° C. or below, 200° C. or below, 175° C. or below, 150° C. or below, 125° C. or below, 100° C. or below, 90° C. or below, 85° C. or below, 80° C. or below, 75° C. or below, 70° C. or below, 65° C. or below, 60° C. or below, 55° C. or below, or 50° C. or below). Typically, the anhydride regeneration reaction temperature is performed at 30° C. or more (e.g., 40° C. or more, 50° C. or more, 60° C. or more, 70° C. or more, 80° C. or more, 90° C. or more, 100° C. or more, 125° C. or more, 150° C. or more, 175° C. or more, or 200° C. or more). Any two of the foregoing endpoints can be used to define a close-ended range, or a single endpoint can be used to define an open-ended range.

The anhydride regeneration reaction can be run under any suitable pressure and typically is run at atmospheric pressure (about 1 atm) or reduced pressure. In some embodiments the pressure typically is lower to help facilitate water removal at reasonable temperatures, such as 0.01 atm (1 kPa) or more (e.g., 0.02 atm (2 kPa) or more, 0.05 atm (5 kPa) or more, 0.07 (7 kPa) atm or more, 0.1 atm (10 kPa) or more, 0.2 atm (20 kPa) or more, 0.5 atm (51 kPa) or more, 0.8 atm (81 kPa) or more, 1 atm (101 kPa) or more and/or 5 atm (507 kPa) or less, 2 atm (203 kPa) or less, 1 atm (101 kPa) or less, 0.8 atm (81 kPa) or less, 0.5 atm (507 kPa) or less, 0.2 atm (20 kPa) or less, or 0.1 atm (10 kPa) or less). Any two of the foregoing endpoints can be used to define a close-ended range, or a single endpoint can be used to define an open-ended range.

The method has a high selectivity in that minimal byproducts are detected beyond the expected products. For example, the term "high selectivity" means that 85 mol % or more (e.g. 87 mol % or more, 89 mol % or more, 90 mol % or more, 92 mol % or more, 94 mol % or more, 95 mol % or more, 96 mol % or more, 97 mol % or more, 98 mol % or more, or 99 mol % or more) in any conversion observed to form the desired product(s).

Figure 3:
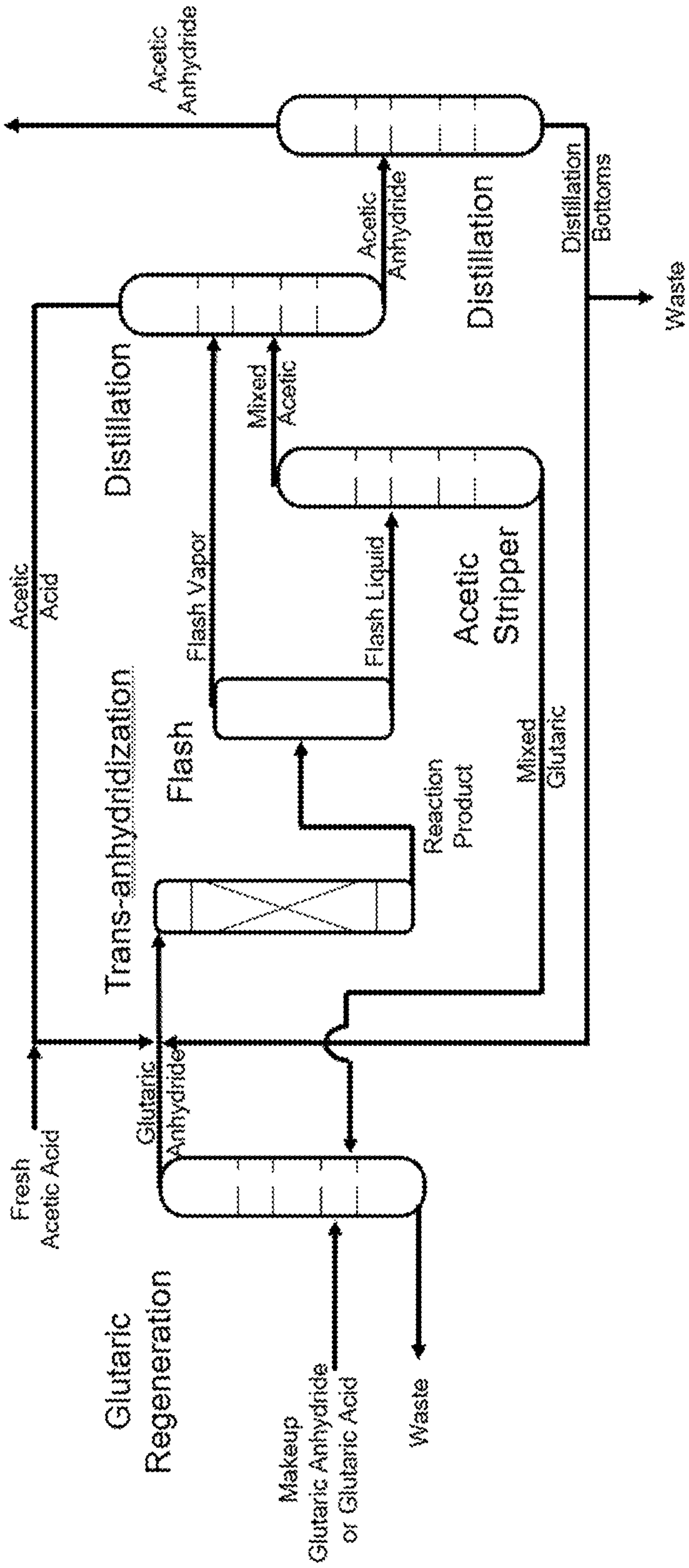
FIG. 3 is a process flow diagram showing the production of acetic anhydride from glutaric anhydride and acetic acid.

In a preferred example of the inventive method, the anhydride is glutaric anhydride, the organic mono-acid is acetic acid, and the anhydride of the monocarboxylic acid is acetic anhydride. An example of the process of producing acetic anhydride using glutaric anhydride as the regenerable anhydride and acetic acid is shown in FIG. 3.

The inventive method for producing an anhydride can be integrated with other processes, particularly processes that either use an organic mono-acid or anhydride as a feedstock or those that produce an organic mono-acid and/or acid anhydride. Thus, the invention provides a first process of producing an anhydride of an organic mono-acid comprising performing a transanhydridization reaction of an organic mono-acid and a thermally regenerable anhydride to produce the anhydride of the organic mono-acid and an acid of the thermally regenerable anhydride, wherein at least one of the organic mono-acid and thermally regenerable anhydride is provided by a preprocess that is integrated with the first process. The transanhydridization process is as described herein. In some embodiments, a partially hydrolyzed thermally regenerable anhydride is formed in addition to the acid of the thermally regenerable anhydride.

In a preferred embodiment of the process, the organic mono-acid is provided by an integrated preprocess.

The preprocess can be upstream, downstream, or parallel to the transanhydridization process (first process). Typically, the transanhydridization process (first process) is integrated with one preprocess, but in some situations, additional processes that use organic mono-acid and/or anhydride can be further integrated. For example, there can be one or more, 2 or more, 3 or more, or 4 or more (e.g., 1, 2, 3, 4, or 5) processes that are integrated either upstream, downstream, and/or in parallel with the transanhydridization process (first process).

In some embodiments, the preprocess is one that uses an anhydride, such as acetic anhydride, as a reactant. In such preprocesses, the products typically are at least one desired product and the acid of the anhydride. Suitable preprocesses include, for example, a cellulose ester process, an acetylated wood process, a tetraacetylethylenediamine (TAED) production process, an aspirin production process, a polymer production process (e.g., a vinyl acetate monomer preprocess, a methyl acetate production preprocess, a polyvinyl acetate production preprocess), and a petrochemical production process.

The process comprises providing a preprocess comprising reacting the anhydride of the organic mono-acid with a feedstock to produce a desired product and an organic mono-acid by-product stream; separating the desired product and organic mono-acid by-product stream; using the separated organic mono-acid by-product stream in the transanhydridization reaction to produce the anhydride of the organic mono-acid and the acid of the thermally regenerable anhydride; separating the anhydride of the organic mono-acid and the acid of the thermally regenerable anhydride; recycling the anhydride of the organic mono-acid to the preprocess; heating the acid of the thermally regenerable anhydride to produce thermally regenerable anhydride; and recycling the regenerated thermally regenerable anhydride for the transanhydridization reaction. The separated organic mono-acid by-product stream can be used "as is" or can be further purified to reduce the concentration of or remove any additional components that may be present. The term "reduce the concentration of," as used herein, means that the concentration of one or more additional components (e.g., 1, 2, 3, 4, or 5 additional components) is reduced by 10% or more (e.g., 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, 97% or more, 98% or more, or 99% or more) relative to the concentration of that component prior to removal. In certain preferred embodiments, the separated organic mono-acid by-product stream is used without further purification.

In any of the integrated processes described herein, the organic mono-acid by-product stream comprises a carboxylic acid, a sulfonic acid, a sulfinic acid, a phosphonic acid, or a phosphinic acid, as described herein. In a preferred embodiment, the organic mono-acid by-product stream comprises a $C_{1-18}$ monocarboxylic acid (e.g., formic acid, acetic acid, propionic acid, butanoic acid (butyric acid), isobutyric acid, pentanoic acid (valeric acid), hexanoic acid (caproic acid), heptanoic acid, octanoic acid (caprylic acid), nonanoic acid (pelargonic acid), decanoic acid (capric acid), undecanoic acid (undecylic acid), dodecanoic acid (lauric acid), tridecanoic acid (tridecylic acid), tetradecanoic acid (myristic acid), pentadecanoic acid (pentadecylic acid), hexadecanoic acid (palmitic acid), heptadecanoic acid (margaric acid), octadecanoic acid (stearic acid), or a combination thereof). In other preferred embodiments, the organic mono-acid is acetic acid, propionic acid, butanoic acid (butyric acid), isobutyric acid, triflic acid, trifluoroacetic acid, maleic acid, or a combination thereof. Preferably, the organic mono-acid is acetic acid.

In some aspects, the integrated preprocess produces a $C_{1-4}$ acid organic monoacid by-product stream (e.g., acetic acid, propionic acid, n-butyric acid, i-butyric acid, or a mixture thereof) from the anhydride reagent. The process comprises providing a preprocess that produces a desired product and a $C_{1-4}$ organic mono-acid by-product stream; separating the desired product and the $C_{1-4}$ organic mono-acid by-product stream; using the separated $C_{1-4}$ organic mono-acid by-product stream and glutaric anhydride in the transanhydridization reaction to produce the anhydride of the $C_{1-4}$ organic mono-acid and glutaric acid; separating the anhydride of the $C_{1-4}$ organic mono-acid and the glutaric acid; recycling the anhydride of the $C_{1-4}$ organic mono-acid to the preprocess as a reagent; heating the glutaric acid to produce regenerated glutaric anhydride; and recycling the regenerated glutaric anhydride for the transanhydridization reaction. In some embodiments of this method, the preprocess is a cellulose ester process, a polymer production process, or a petrochemical production process.

In an example, the integrated preprocess is a cellulose ester process, such as a cellulose acetate process. For example, a cellulose acetate process includes the acetylation of cellulose with acetic anhydride. The process produces cellulose acetate, a biodegradable polymer used in, e.g., textiles and high absorbency products, and acetic acid as a by-product. The cellulose can be from any suitable source, including a plant source (e.g., cotton, hemp, flax, jute, bagasse, and sugar cane stalk) and wood. The cellulose ester process can include a catalyst, such as mineral acid (e.g., sulfuric acid, hydrochloric acid, hydrobromic acid, hydroiodic acid, perchloric acid, boric acid, nitric acid, nitrous acid, and/or phosphoric acid). In addition, the cellulose ester process can include a pretreatment with a suitable base (e.g., sodium hydroxide, potassium hydroxide) prior to acetylation.

Accordingly, the process comprises providing a preprocess that produces a cellulose ester product and a $C_{1-4}$ organic mono-acid by-product stream (e.g., acetic acid, propionic acid, n-butyric acid, i-butyric acid, or a mixture thereof); separating the cellulose ester product and the $C_{1-4}$ organic mono-acid by-product stream; using the separated $C_{1-4}$ organic mono-acid by-product stream and glutaric anhydride in the transanhydridization reaction to produce the anhydride of the $C_{1-4}$ organic mono-acid and glutaric acid; separating the anhydride of the $C_{1-4}$ organic mono-acid and the glutaric acid into separate streams; recycling the anhydride of the $C_{1-4}$ organic mono-acid to the preprocess as a reagent; heating the glutaric acid to produce regenerated glutaric anhydride; and recycling the regenerated glutaric anhydride for the transanhydridization.

In the cellulose ester process, the $C_{1-4}$ organic mono-acid by-product stream typically comprises acetic acid, however, in some aspects of the process, the $C_{1-4}$ organic mono-acid by-product stream comprises a $C_{2-4}$ organic mono-acid. The $C_{1-4}$ organic mono-acid by-product stream can optionally further comprise the anhydride of the $C_{1-4}$ organic mono-acid and/or a mineral acid (e.g., sulfuric acid, hydrochloric acid, hydrobromic acid, hydroiodic acid, perchloric acid, boric acid, nitric acid, nitrous acid, and/or phosphoric acid).

In some embodiments of the integrated cellulose ester process, the stream comprising the anhydride of the $C_{1-4}$ organic mono-acid product from the transanhydridization reaction can further comprise unreacted $C_{1-4}$ organic mono-acid. The unreacted $C_{1-4}$ organic mono-acid can be separated, if desired, or left with the anhydride product.

In an example, the integrated preprocess is an acetylated wood process. In an acetylated wood process, untreated wood (e.g., wood with a moisture content typically at 6 wt % or below) is soaked in acetic anhydride which serves to acetylate at least some of the free hydroxyls in the ligno-cellulosic groups of wood, leaving acetic acid as a by-product. The acetylated wood product has reduced water absorption, which provides improved dimensional stability (less shrinkage), hardness, and durability.

For example, the process comprises providing a preprocess using acetic anhydride to produce an acetylated wood product and an acetic acid by-product stream; separating the acetylated wood product and the acetic acid by-product stream; using the separated acetic acid by-product stream and glutaric anhydride in the transanhydridization reaction to produce acetic anhydride and glutaric acid; separating the acetic anhydride and glutaric acid; recycling the acetic anhydride to the preprocess as a reagent; heating the glutaric acid to produce regenerated glutaric anhydride; and recycling the regenerated glutaric anhydride for the transanhydridization reaction.

In some aspects of this integrated process, the separated acetic acid by-product stream can further comprise at least one additional component selected from acetic anhydride, a terpene, a chloride-containing compound, a mineral acid, and a combination of any of the foregoing. For example, the separated acetic acid by-product stream can further comprise at least one terpene and/or at least one chloride-containing compound. If desired, at least one additional component (e.g., the at least one terpene and/or the at least one chloride-containing compound) can be at least partially removed from the separated acetic acid by-product stream prior to the transanhydridization reaction. The term "at least partially removed" means that the concentration of one or more additional components (e.g., 1, 2, 3, 4, or 5 additional components) is reduced by 10% or more (e.g., 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, 97% or more, 98% or more, or 99% or more) relative to the concentration of that component prior to removal. The separation can take place by any suitable method, including methods described herein (e.g., azeotropic distillation, passing the separated acetic acid by-product stream through an activated carbon bed or other resin, extraction, and/or ozonolysis).

Production processes that use acetic anhydride as a raw material often produce a byproduct stream that contains one or more acetyl compounds. These acetyl-containing streams can contain a mixture of acetic acid, unreacted acetic anhydride, and various other organic and inorganic compounds. For example, the acetyl-containing byproduct stream from a wood acetylation process can contain acetic acid, acetic anhydride, terpenes, chlorinated organics, and various other organic materials extracted from wood.

The acetyl-containing streams from other production processes can be utilized as a feedstock for the anhydride production process described herein to convert acid to anhydride. In some instances it may be desired to perform separation and/or purification steps on the acetyl-containing stream before feeding at least a portion of it to the anhydride production process. The separation steps can use any suitable method of physical separation, including distillation and extraction. Species can also be removed or transformed by reactive chemistries, such as selective oxidation and/or thermal degradation of certain species. This includes catalytic and/or non-catalytic reactions. Oxidation reactions can include the wet air oxidation (WAO) process. The WAO process comprises contacting the acetyl-containing stream with oxygen at elevated temperature and pressure. WAO can be used to convert organic species to carbon dioxide, water, and short chain organic acids. Components, such as sulfides, cyanides, and chlorinated organics, can also be oxidized. The WAO process can involve any or all of the following reactions:

$$\text{Organics}+O_2\rightarrow CO_2+H_2O+RCOOH^*$$

$$\text{Sulfur Species}+O_2\rightarrow SO_4^{-2}$$

$$\text{Organic Cl}+O_2\rightarrow Cl^{-1}+CO_2+RCOOH^*$$

$$\text{Organic N}+O_2\rightarrow NH_3+CO_2+RCOOH^*$$

$$\text{Phosphorus}+O_2\rightarrow PO_4^{-3}$$

*Short chain organic acids, such as acetic acid, are typically the majority of residual organic compounds.

In some instances, additional separation and/or purification steps can be performed within the anhydride production process in order to remove components introduced from the acetyl-containing feedstock. These steps can include a subset of the physical and reactive methods mentioned above.

Further provided is a process comprising a wood acetylation process coupled to an acetic anhydride production process, wherein the wood acetylation process comprises subjecting wood to acetylation comprising an acetylation fluid, and the acetic anhydride production process comprises performing a transanhydridization reaction between acetic acid and a thermally regenerable anhydride to produce an acetic anhydride reaction fluid comprising acetic anhydride and acetic acid, wherein the raw (i.e., unprocessed; including at least 0.5% of acetic acid and optionally one or more impurities) acetic anhydride reaction fluid is used in the wood acetylation process as an acetylation fluid. In some aspects of this process, the process further comprises recovering acetylation fluid from the wood acetylation process to obtain recovered acetylation fluid comprising acetic acid and acetic anhydride; and distilling the recovered acetylation fluid to obtain acetic acid by-product that is used as a reactant in the transanhydridization reaction.

The invention also provides an integrated wood acetylation and anhydride production system comprising

- a wood acetylation vessel for receiving wood and an acetylation fluid that is in fluid communication with a first fluid channel for conveying recovered acetylation fluid;
- a first separation vessel for receiving the recovered acetylation fluid from the first fluid channel and that is in fluid communication with a recovered acetic anhydride vessel and an acetic acid by-product vessel;

a transanhydridization vessel for receiving acetic acid by-product and a thermally regenerable anhydride that is in fluid communication with
(a) the acetic acid by-product vessel; and
(b) a second fluid channel for conveying the thermally regenerable anhydride;
a third fluid channel for conveying acetic anhydride and an acid of the thermally regenerable anhydride to a second separation vessel;
a fourth fluid channel for conveying separated acetic anhydride from the second separation vessel to a first anhydride vessel;
a fifth fluid channel for conveying separated acid of the thermally regenerated anhydride from the first separation vessel to a regeneration vessel;
wherein
the first anhydride vessel is in fluid communication with the wood acetylation vessel; and
the regeneration vessel is in fluid communication with the second fluid channel.

Figure 4A:
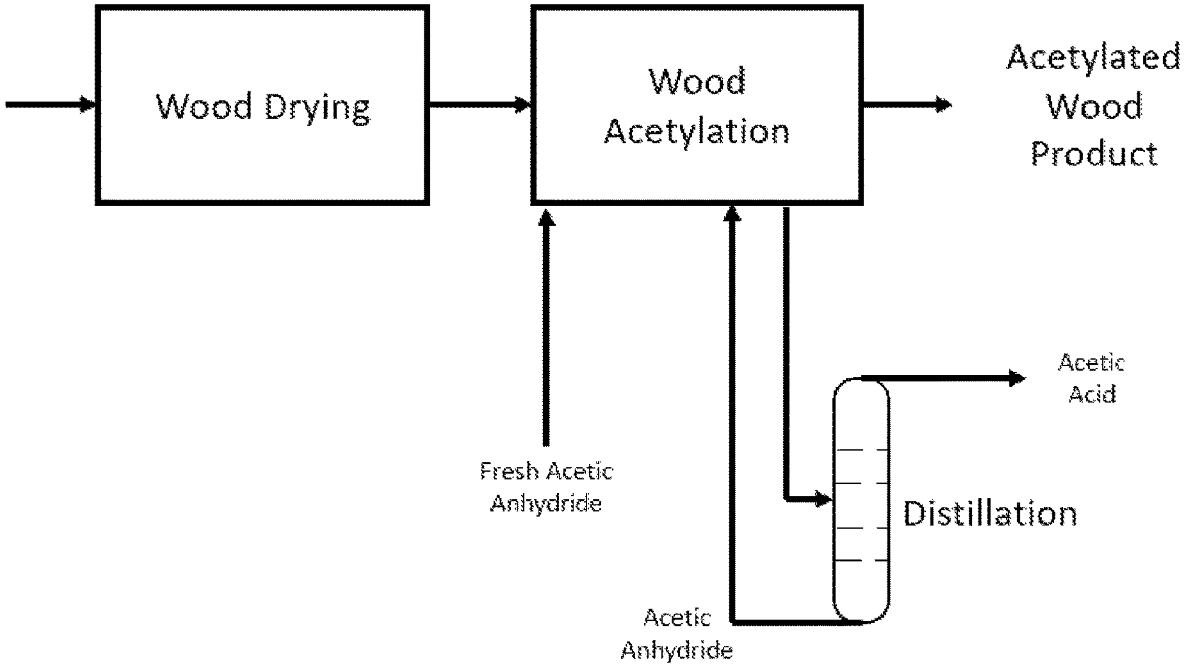
FIGS. 4A-B are schematics of an integrated anhydride production process and an acetylated wood process.
Figure 4B:
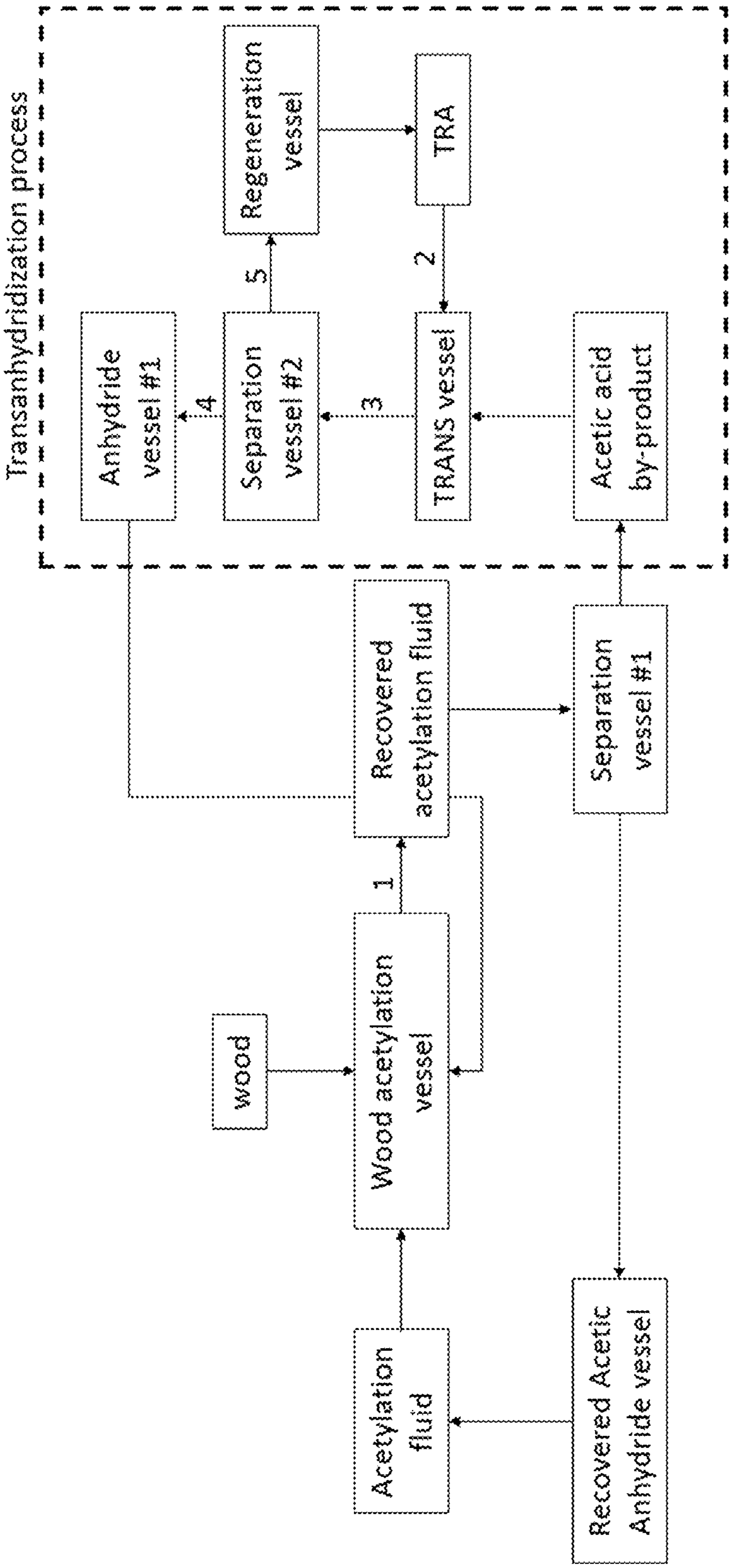
Figure 4C:
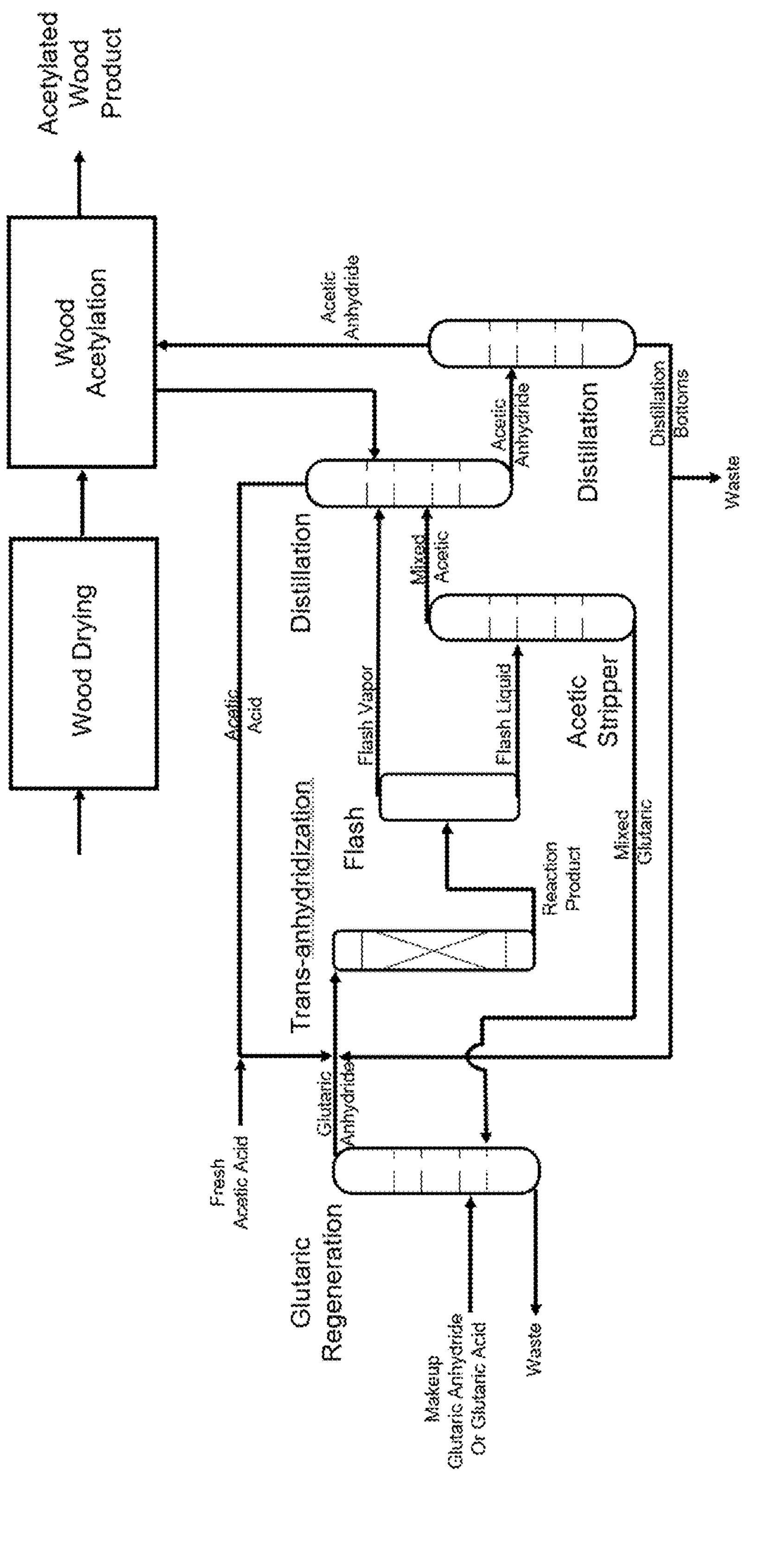
FIGS. 4C and 4D are process flow diagrams of the integrated processes.
Figure 4D:
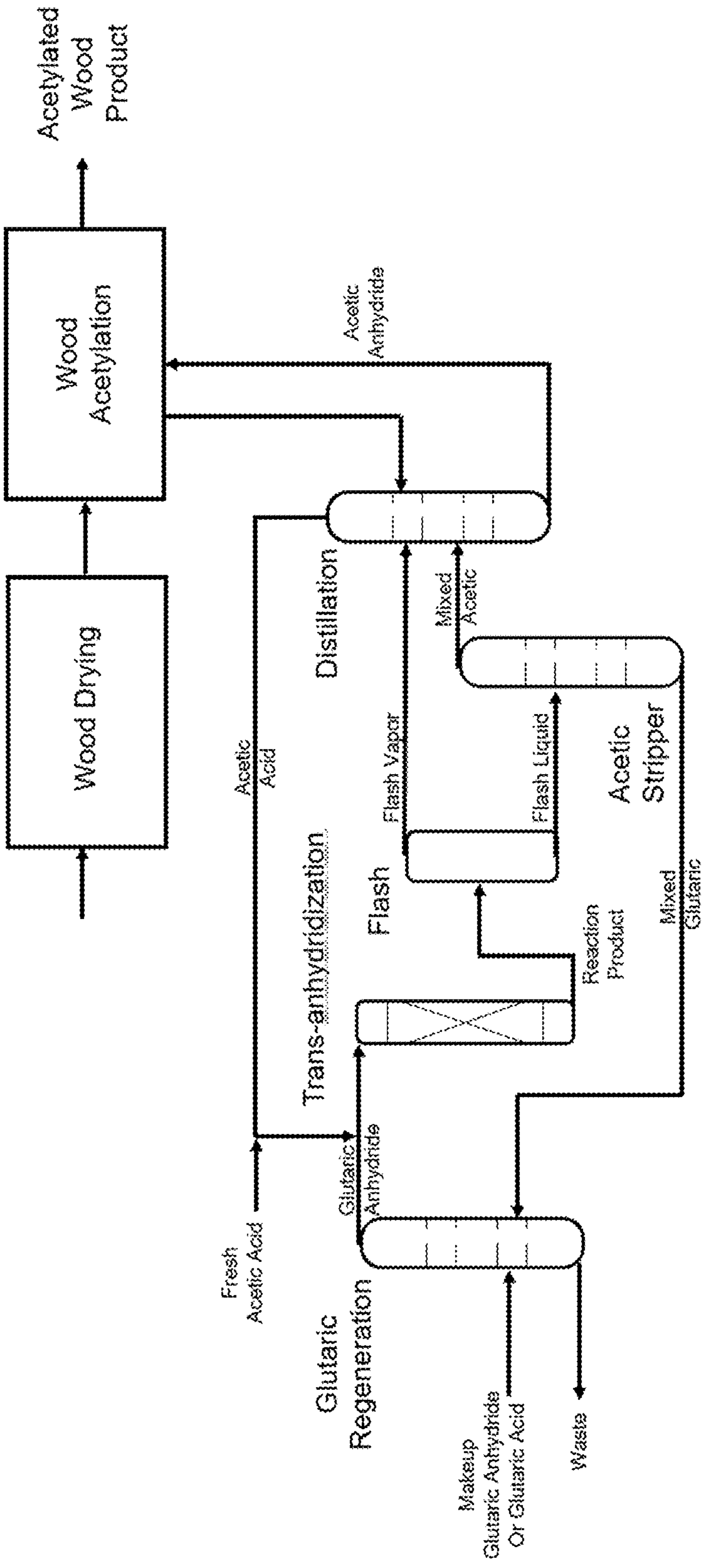

FIG. 4A is a schematic showing the wood acetylation process of the prior art. Schematics showing the anhydride production process integrated with an acetylated wood process is shown in FIGS. 4B, 4C, and 4D.

Further provided is a process of supplying an acetic acid reactant feed to a transanhydridization reaction unit, in which at least a portion of the acetic acid reactant feed is acetylation fluid that has been recovered from a wood acetylation process, such as a process described herein, and which comprises acetic acid and acetic anhydride. In an embodiment, at least a portion of the acetic anhydride is separated and recovered, and the remaining acetylation fluid comprising primarily (e.g., 50% or more) acetic acid is provided to the transanhydridization reaction. In an aspect of this process, the transanhydridization reaction unit produces acetic anhydride from acetic acid from the acetic acid reactant feed and a thermally regenerable anhydride, as described herein.

The acetic acid reactant feed in the integrated wood acetylation and anhydride production system can comprise any suitable amount of acetic acid, but typically comprises at least 25% (e.g., 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, 97% or more, or 99% or more) acetic acid. While the acetic acid reactant feed can comprise 100% acetic acid, typically the acetic acid reactant feed further comprises at least one additional component such that the acetic acid reactant feed comprises 99% or less (e.g., 97% or less, 95% or less, 90% or less, 85% or less, 80% or less, 75% or less, 70% or less, 65% or less, 60% or less, 55% or less, 50% or less, 45% or less, 40% or less, 35% or less, or 30 or less) acetic acid. Any two of the foregoing endpoints can be used to define a close-ended range, or a single endpoint can be used to define an open-ended range. The at least one additional component typically is selected from acetic anhydride, a terpene, a chloride-containing compound, a mineral acid, or a combination of any of the foregoing. For example, the acetic acid reactant feed can further comprise at least one terpene and/or at least one chloride-containing compound.

In an embodiment of this process, the acetic acid reactant feed comprises at least 10% by volume, at least 20% by volume, at least 25% by volume, at least 30% by volume, at least 40% by volume, at least 50% by volume, at least 60% by volume, at least 70% by volume, at least 75% by volume, at least 80% by volume, at least 90% by volume, or at least 95% by volume of the acetic acid by-product stream.

In an embodiment of this process, there is a purge on the acetic acid reactant feed stream which comprises less than 50% by volume, less than 40% by volume, less than 30% by volume, less than 25% by volume, less than 20% by volume, less than 10% by volume, less than 6% by volume, less than 5% by volume, less than 4% by volume, less than 3% by volume, less than 2% by volume, or less than 1% by volume of the total volumetric flow of the acetic acid reactant feed stream.

In an embodiment of this process, the purge stream can undergo treatment to reduce the concentration of an additional component selected from acetic anhydride, a terpene, a chloride-containing compound, and a mineral acid. In a further embodiment of this process, the purge stream can be reintroduced into the acetic acid reactant feed stream after undergoing said treatment.

In an embodiment of this process, the acetic acid reactant feed comprises at least 20 ppm (e.g., 20 ppm or more, 30 ppm or more, 50 ppm or more, 100 ppm or more, 200 ppm or more, 300 ppm or more, 400 ppm or more, 500 ppm or more, 600 ppm or more, 700 ppm or more, 800 ppm or more, 900 ppm or more, 1,000 ppm or more, 1,500 ppm or more, 2,000 ppm or more, 2,500 ppm or more, 3,000 ppm or more, 3,500 ppm or more, 4,000 ppm or more, 5,000 ppm or more, 5,500 ppm or more, or 6,000 ppm or more) of terpenes. Alternatively, or in addition, the acetic acid reactant feed can comprise 6,000 ppm or less (e.g., 5,500 ppm or less, 5,000 ppm or less, 4,500 ppm or less, 4,000 ppm or less, 3,500 ppm or less, 3,000 ppm or less, 2,500 ppm or less, 2,000 ppm or less, 1,500 ppm or less, 1,000 ppm or less, 900 ppm or less, 800 ppm or less, 700 ppm or less, 600 ppm or less, 500 ppm or less, 400 ppm or less, 300 ppm or less, 200 ppm or less, 100 ppm or less, or 50 ppm or less) of terpenes. Any two of the foregoing endpoints can be used to define a close-ended range, or a single endpoint can be used to define an open-ended range. For example, the acetic acid reactant feed can comprise 20 ppm or more and 6,000 ppm or less of terpenes.

In an example, the integrated preprocess is a tetraacetylethylenediamine (TAED) production process. In a TAED process, ethylenediamine is acetylated with acetic anhydride to produce diacetylethylenediamine (DAED), which is further reacted with acetic anhydride to produce TAED and acetic acid as a by-product. TAED typically is an environmentally safe bleaching agent that can be used in laundry detergent, dishwasher detergent, dental cleanser, and other cleaners.

For example, the process comprises providing a preprocess using acetic anhydride to produce a tetraacetylethylenediamine (TAED) product and an acetic acid by-product stream; separating the tetraacetylethylenediamine product and the acetic acid by-product stream; using the separated acetic acid by-product stream and glutaric anhydride in the transanhydridization reaction to produce acetic anhydride and glutaric acid; separating the acetic anhydride and glutaric acid; recycling the acetic anhydride to the preprocess as a reagent; heating the glutaric acid to produce regenerated glutaric anhydride; and recycling the regenerated glutaric anhydride for the transanhydridization. The acetic acid by-product stream can further comprise unreacted acetic anhydride, which can optionally be separated from the acetic acid by-product stream.

In embodiments of this integrated process, any unreacted acetic acid from the transanhydridization reaction can be separated and routed back to the transanhydridization reaction and/or routed to a diacetylethylenediamine (DAED) reactor.

Figure 5:
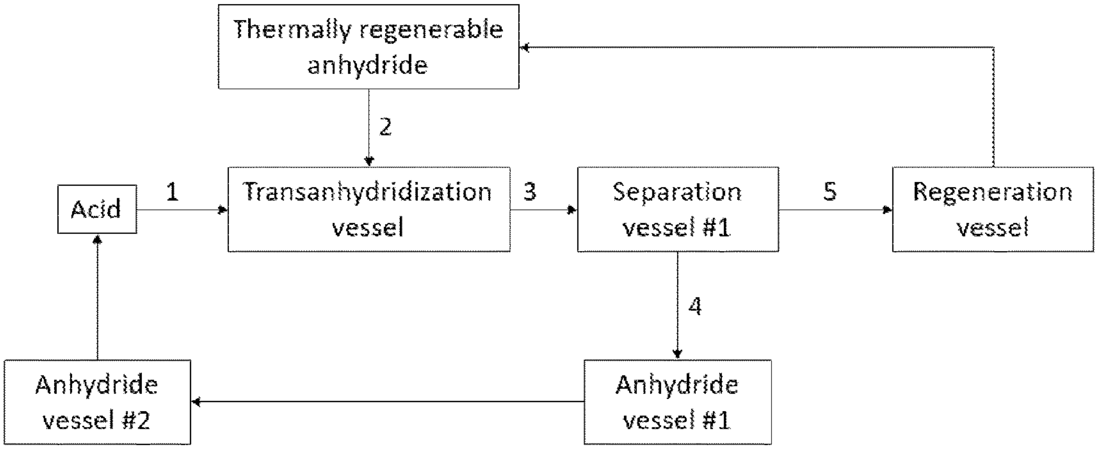
FIG. 5 is a schematic of an integrated process showing a transanhydridization vessel for receiving an organic mono-acid and a thermally regenerable anhydride that is in fluid communication with (a) a first fluid channel for conveying organic mono-acid and (b) a second fluid channel for conveying thermally regenerable anhydride; a third fluid channel for conveying an anhydride of the organic mono-acid and an acid of the thermally regenerable anhydride to separation vessel #1, a fourth fluid channel for conveying separated anhydride of the organic mono-acid from separation vessel #1 to anhydride vessel #1; a fifth fluid channel for conveying separated acid of the thermally regenerated anhydride from separation vessel #1 to a regeneration vessel. Anhydride vessel #1 is in fluid communication with an integrated system for reacting the separated anhydride of the organic mono-acid. The system comprises anhydride vessel #2 for receiving fresh anhydride of the organic mono-acid in the integrated system and that is in fluid communication with the first fluid channel. The regeneration vessel is in fluid communication with the second fluid channel.

With respect to integrated processes that rely on using an anhydride as a reagent, the invention provides an anhydride production system comprising a transanhydridization vessel for receiving an organic mono-acid and a thermally regenerable anhydride that is in fluid communication with (a) a first fluid channel for conveying the organic mono-acid and (b) a second fluid channel for conveying the thermally regenerable anhydride; a third fluid channel for conveying an anhydride of the organic mono-acid and an acid of the thermally regenerable anhydride to a first separation vessel, a fourth fluid channel for conveying separated anhydride of the organic mono-acid from the first separation vessel to a first anhydride vessel; a fifth fluid channel for conveying separated acid of the thermally regenerated anhydride from the first separation vessel to a regeneration vessel; wherein the first anhydride vessel is in fluid communication with an integrated system for reacting the separated anhydride of the organic mono-acid; a second anhydride vessel for receiving fresh anhydride of the organic mono-acid in the integrated system is in fluid communication with the first fluid channel; and the regeneration vessel is in fluid communication with the second fluid channel. See the schematic of FIG. 5.

Figure 6:
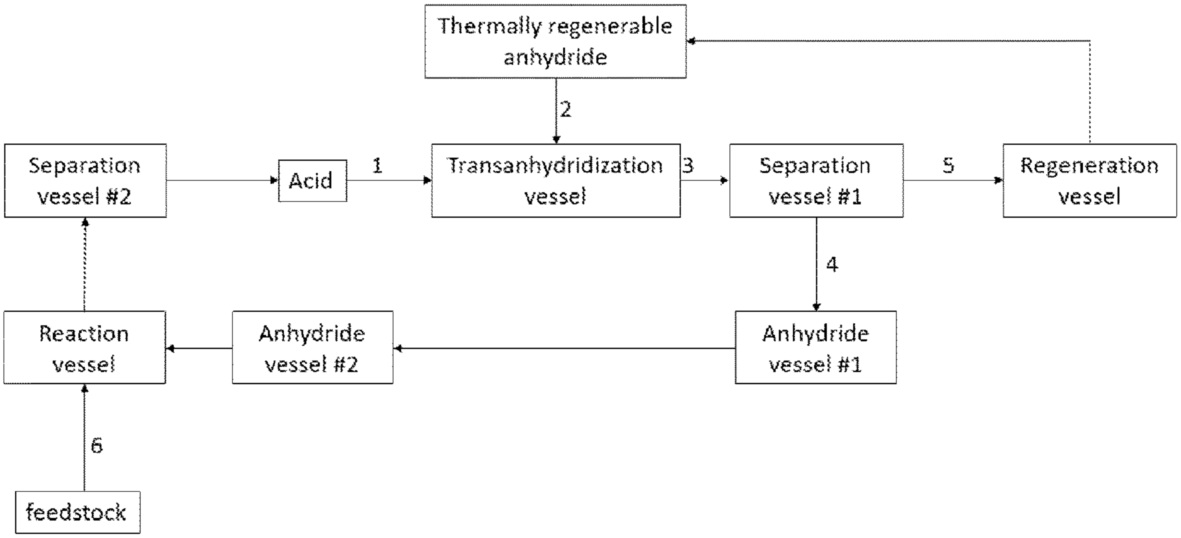
FIG. 6 is a schematic similar to that shown in FIG. 5 and further shows anhydride vessel #2 in fluid communication with a reaction vessel, the reaction vessel is in fluid communication with (a) a sixth fluid channel for conveying feedstock and (b) separation vessel #2. The second separation vessel is in fluid communication with the first fluid channel, and anhydride vessel #1 is in fluid communication with anhydride vessel #2 and/or the reaction vessel.
Figure 7:
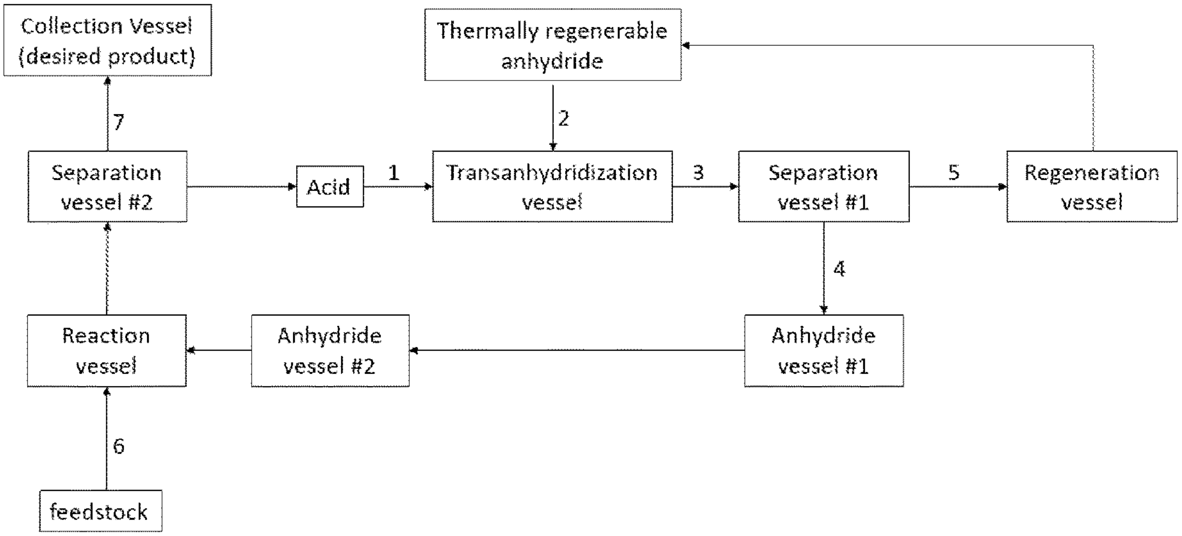
FIG. 7 is a schematic similar to that shown in FIG. 6 and further shows that separation vessel #2 can comprise a seventh fluid channel for conveying a desired product other than the organic mono-acid to a collection vessel.

In some embodiments of the anhydride production system: the second anhydride vessel is in fluid communication with a reaction vessel, the reaction vessel is in fluid communication with (a) a sixth fluid channel for conveying feedstock and (b) a second separation vessel, the second separation vessel is in fluid communication with the first fluid channel, and the first anhydride vessel is in fluid communication with the second anhydride vessel or the reaction vessel. See the schematic of FIG. 6. The second separation vessel can comprise a seventh fluid channel for conveying a desired product other than the organic mono-acid, such as a cellulose ester (e.g., cellulose acetate) product, an acetylated wood product, or a tetraacetylethylenediamine (TAED) product, to a collection vessel. See the schematic of FIG. 7.

In some embodiments, the integrated preprocess is one that yields an anhydride, such as acetic anhydride, as a product. Suitable preprocesses include, for example, an anhydride production preprocess (e.g., a ketene process or a carbonylation process) or a vinyl acetate monomer preprocess. In such preprocesses, the acid of the anhydride typically is used as an excess reagent, and the remaining unreacted acid from the preprocess serves as the reagent in the transanhydridization reaction. The separated excess acetic acid reagent stream can be used "as is" or can be further purified to reduce the concentration of or to remove any additional components that may be present. In certain preferred embodiments, the separated excess acetic acid reagent stream is used without further purification.

In an example, the integrated preprocess is a ketene preprocess, which includes dehydrating acetic acid to produce ketene (ethenone: $H_2C{=}C{=}O$) and water. Gaseous ketene is removed and then reacted with more acetic acid to form acetic anhydride. The process typically requires a catalyst (e.g., triethyl phosphate) and high reaction temperatures (e.g., 700 to 750° C.). In a distillation column, crude acetic anhydride is distilled and recovered as the bottom product, whereas the top product is unreacted acetic acid.

In a specific example, the process comprises providing a ketene preprocess that produces acetic anhydride and excess acetic acid reagent; separating the acetic anhydride and the excess acetic acid reagent into streams; using the separated excess acetic acid reagent stream and glutaric anhydride in the transanhydridization reaction to produce acetic anhydride and glutaric acid; separating the acetic anhydride and glutaric acid; combining the acetic anhydride produced from the transanhydridization with the acetic anhydride produced in the ketene preprocess; heating the glutaric acid to produce regenerated glutaric anhydride; and recycling the regenerated glutaric anhydride for the transanhydridization. In some embodiments, the process further comprises recycling unreacted acetic acid from the transanhydridization reaction back to one of, or to both the transanhydridization reaction and the ketene preprocess.

In some embodiments, the integrated ketene preprocess that produces acetic anhydride and excess acetic acid reagent can comprise a third anhydride production process. For example, butyric anhydrides are produced commercially by the reaction of butyric acid with excess acetic anhydride. See, for example, the methods described in U.S. Pat. Nos. 3,513,180 and 2,163,013, each of which is incorporated herein in its entirety. Generally, the process comprises separating acetic anhydride produced in the ketene preprocess and the excess acetic acid reagent into streams; using the separated acetic acid by-product stream and glutaric anhydride in the transanhydridization reaction to produce acetic anhydride and glutaric acid; separating the acetic anhydride and glutaric acid; recycling the acetic anhydride to a third anhydride production process for producing $C_{3-4}$ anhydride; heating the glutaric acid to produce regenerated glutaric anhydride; and recycling the regenerated glutaric anhydride for the transanhydridization reaction. The process can further comprise reacting the acetic anhydride from the transanhydridization reaction with $C_{3-4}$ organic mono-acid to produce the corresponding anhydride and acetic acid in the third anhydride production process; and recycling the acetic acid produced in the third anhydride production process back to the ketene preprocess and/or the transanhydridization reaction.

In an example, the integrated preprocess is a carbonylation preprocess, which involves the reaction of methanol (e.g., the Monsanto process) or methyl acetate (e.g., the Tennessee Eastman acetic anhydride process) with carbon monoxide. The methyl acetate can be produced by esterifying methanol with acetic acid. The carbonylation preprocess can further comprises other components, including a catalyst, such as a metal (e.g., rhodium, nickel, iridium, zirconium) catalyst, a co-promoter (e.g., methyl iodide, N,N-dimethyl imidazolium iodide), an iodide salt (e.g., an alkali metal salt, a quaternary ammonium salt, or a quaternary phosphonium salt), a phosphine, and/or hydrogen gas. The carbonylation preprocess typically operates at a pressure of 10-60 atm (1013-6080 kPa) and a temperature of about 150-200° C.

Accordingly, the process comprises providing a carbonylation preprocess that produces acetic anhydride and an acetic acid by-product; separating the acetic anhydride and the acetic acid by-product into streams; using the separated acetic acid by-product stream and glutaric anhydride in the transanhydridization reaction to produce acetic anhydride and glutaric acid; separating the acetic anhydride and glutaric acid; combining the acetic anhydride produced from the transanhydridization with the acetic anhydride produced in the carbonylation preprocess; heating the glutaric acid to produce regenerated glutaric anhydride; and recycling the regenerated glutaric anhydride for the transanhydridization. The process of can further comprise recycling unreacted acetic acid back to the transanhydridization reaction.

In an example, the integrated preprocess is a vinyl acetate monomer preprocess that produces vinyl acetate, a precursor to polyvinyl acetate (PVA), and excess acetic acid reagent. In particular, ethylene is reacted with acetic acid and oxygen in the presence of a catalyst (e.g., a palladium catalyst) to form vinyl acetate and water. In an example, the process comprises separating the vinyl acetate monomer and the excess acetic acid reagent from the vinyl acetate monomer preprocess into streams; using the separated excess acetic acid reagent stream and glutaric anhydride in the transanhydridization reaction to produce acetic anhydride and glutaric acid; separating the acetic anhydride and glutaric acid; heating the glutaric acid to produce regenerated glutaric anhydride; and recycling the regenerated glutaric anhydride for the transanhydridization. In some embodiments, methyl acetate is produced as a co-product in the vinyl acetate monomer preprocess, and the methyl acetate is hydrolyzed to provide acetic acid. If desired, acetic acid produced from the hydrolyzed methyl acetate is used as a reagent in the transanhydridization reaction.

In another embodiment of the process, the preprocess can be a PVA production process and/or a methyl acetate production process. For example, vinyl acetate can be converted to PVA using any suitable reaction conditions (e.g., a radical initiator, methanol, a catalyst, etc.). The PVA can be reacted with methanol in the presence of a base to produce PVA and methyl acetate. The methyl acetate can be hydrolyzed under suitable reaction conditions to produce acetic acid. The acetic acid can be recycled back to a vinyl acetate production preprocess, used as a feedstock for a transanhydridization reaction process, each as described herein, or both.

Figure 8:
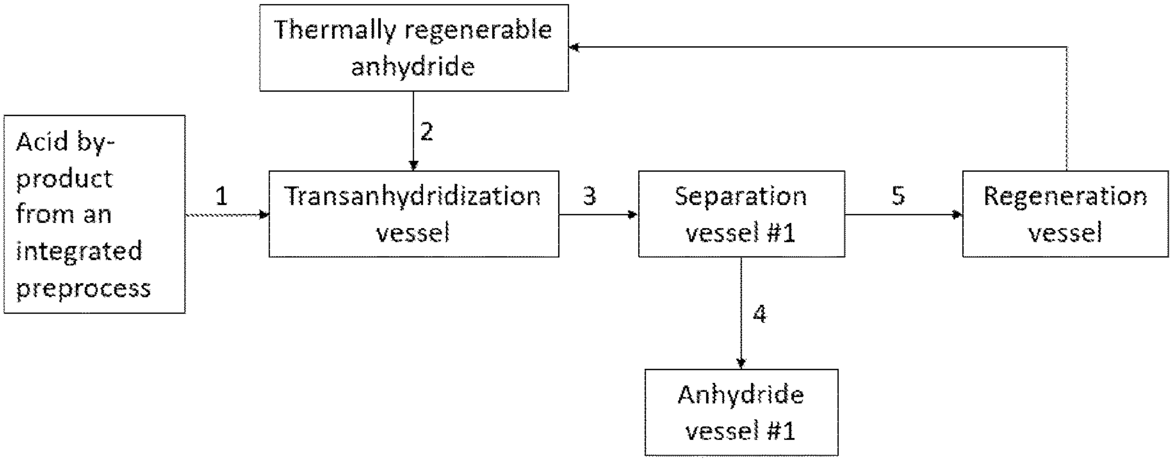
FIG. 8 is a schematic of an integrated process showing a transanhydridization vessel for receiving an organic mono-acid by-product from an integrated preprocess and a thermally regenerable anhydride that is in fluid communication with (a) a first fluid channel for conveying the organic mono-acid by-product that is in fluid communication with the preprocess and (b) a second fluid channel for conveying the thermally regenerable anhydride; a third fluid channel for conveying an anhydride of the organic mono-acid by-product and an acid of the thermally regenerable anhydride to separation vessel #1, a fourth fluid channel for conveying separated anhydride of the organic mono-acid by-product from separation vessel #1 to anhydride vessel #1; a fifth fluid channel for conveying separated acid of the thermally regenerated anhydride from separation vessel #1 to a regeneration vessel; in which the regeneration vessel is in fluid communication with the second fluid channel.

With respect to integrated processes that rely on producing an anhydride as a product, the invention provides an anhydride production system comprising a transanhydridization vessel for receiving an organic mono-acid by-product from an integrated preprocess and a thermally regenerable anhydride that is in fluid communication with (a) a first fluid channel for conveying the organic mono-acid by-product that is in fluid communication with the preprocess and (b) a second fluid channel for conveying the thermally regenerable anhydride; a third fluid channel for conveying an anhydride of the organic mono-acid by-product and an acid of the thermally regenerable anhydride to a first separation vessel, a fourth fluid channel for conveying separated anhydride of the organic mono-acid by-product from the first separation vessel to a first anhydride vessel; a fifth fluid channel for conveying separated acid of the thermally regenerated anhydride from the first separation vessel to a regeneration vessel; wherein the regeneration vessel is in fluid communication with the second fluid channel. See the schematic of FIG. 8. The organic mono-acid by-product is as described herein, e.g., comprises a carboxylic acid (e.g., a $C_{1-18}$ monocarboxylic acid), a sulfonic acid, a sulfinic acid, a phosphonic acid, or a phosphinic acid.

Figure 9:
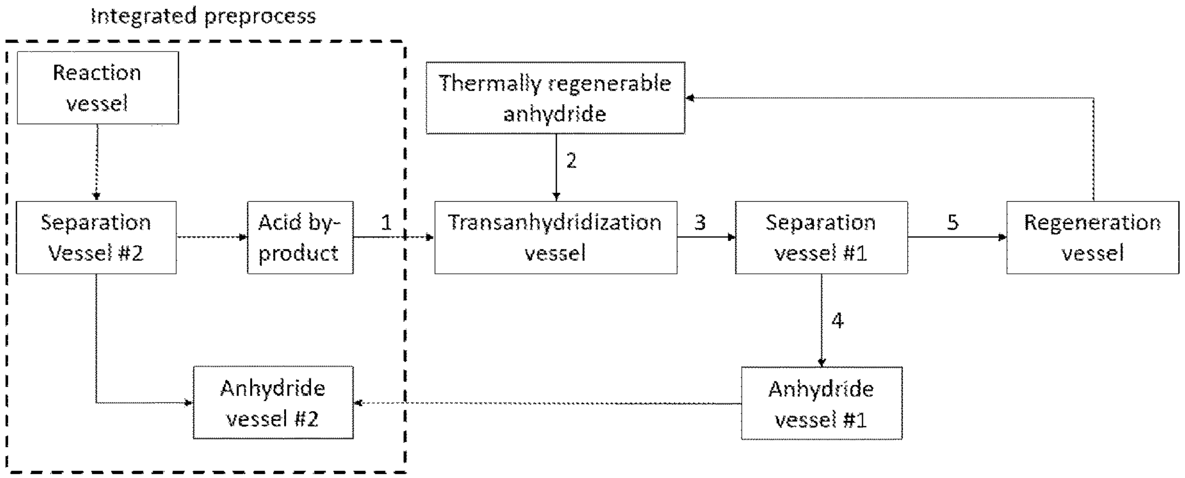
FIG. 9 is a schematic similar to that shown in FIG. 8 and further shows anhydride vessel #1 can be in fluid communication with anhydride vessel #2 for receiving anhydride of the organic mono-acid that is produced in the integrated preprocess and that is in fluid communication with separation vessel #2, in which separation vessel #2 is in fluid communication with (a) a reaction vessel for receiving a mixture of the anhydride of the organic mono-acid and the organic mono-acid by-product and (b) the first fluid channel.

In some embodiments of the anhydride production system, the first anhydride vessel is in fluid communication with an integrated system that produces the anhydride of the organic mono-acid and the organic mono-acid by-product. The anhydride production system can further comprise a second anhydride vessel for receiving anhydride of the organic mono-acid that is produced in the integrated system and that is in fluid communication with a second separation vessel, wherein the second separation vessel is in fluid communication with (a) a reaction vessel for receiving a mixture of the anhydride of the organic mono-acid and the organic mono-acid by-product and (b) the first fluid channel. See the schematic of FIG. 9.

In a particular example of the anhydride production system: the organic mono-acid by-product from an integrated preprocess is acetic acid; the integrated preprocess is a ketene process; the thermally regenerable anhydride is glutaric anhydride; and the anhydride of the organic mono-acid by-product is acetic anhydride.

Figure 10:
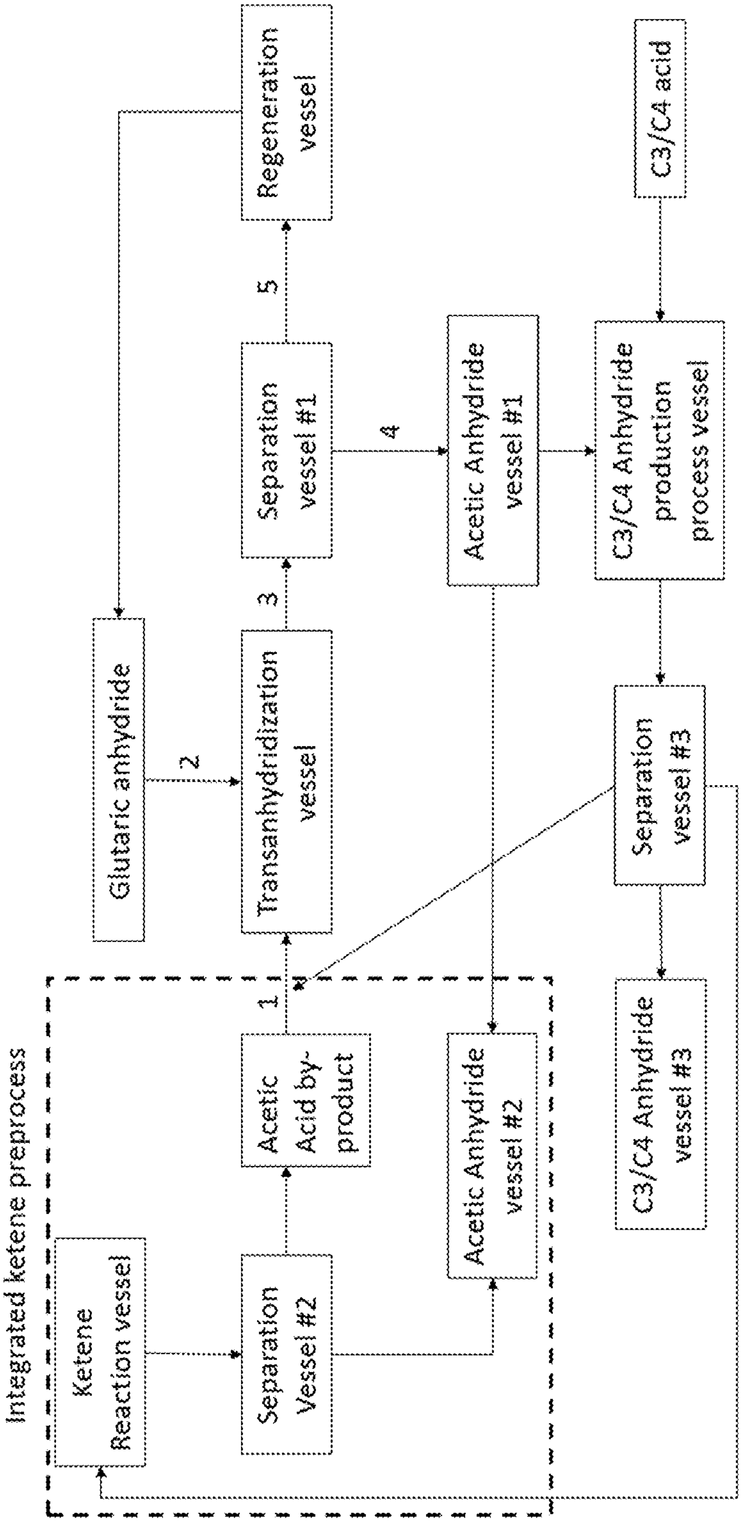
FIG. 10 is a schematic similar to that shown in FIG. 9 and further shows a $C_{3-4}$ anhydride production process vessel for receiving a mixture of acetic anhydride produced in the transanhydridization reaction and a $C_{3-4}$ organic mono-acid that is in fluid communication with separation vessel #3, in which separation vessel #3 is in fluid communication with (a) $C_{3-4}$ anhydride vessel #3 for receiving the anhydride of the $C_{3-4}$ organic mono-acid; and (b) the first fluid channel, the ketene preprocess, or both.
Figure 11:
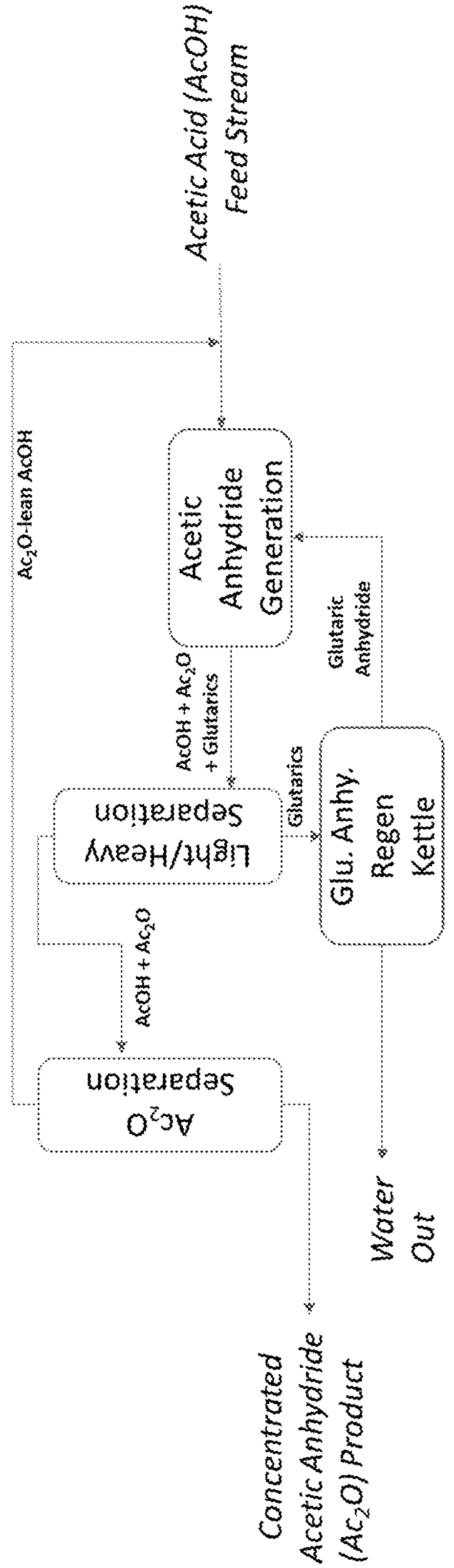
FIG. 11 is a scheme illustrating an acetic acid feed (AcOH) feed and a glutaric anhydride feed to generate acetic anhydride ($Ac_2O$).

If desired, the first anhydride vessel can be in fluid communication with an integrated anhydride production process that produces $C_{3-4}$ anhydride. For example, the anhydride production system can further comprise a third anhydride production process vessel for receiving a mixture of acetic anhydride produced in the transanhydridization reaction and a $C_{3-4}$ organic mono-acid that is in fluid communication with a third separation vessel, wherein the third separation vessel is in fluid communication with (a) a third anhydride vessel for receiving the anhydride of the $C_{3-4}$ organic mono-acid; and (b) the first fluid channel, the ketene preprocess, or both. In some embodiments, the second anhydride vessel is in fluid communication with the third anhydride production process vessel. See the schematic of FIG. 10.

In any of the processes described herein, including an integrated process or anhydride production system, any suitable amount of the organic mono-acid is used relative to the thermally regenerable anhydride in the transanhydridization. For example, 1 or more equivalents of the organic mono-acid is used, such as 2 or more equivalents, 3 or more equivalents, 4 or more equivalents, 5 or more equivalents, 6 or more equivalents, 7 or more equivalents, 8 or more equivalents, 9 or more equivalents, or 10 or more equivalents, relative to the organic mono-acid. Typically, the transanhydridization reaction will use 30 equivalents or less of the organic mono-acid, such as 28 equivalents or less, 25 equivalents or less, 22 equivalents or less, 20 equivalents or less, 18 equivalents or less, 15 equivalents or less, 12 equivalents or less, 10 equivalents or less, 9 equivalents or less, 8 equivalents or less, 7 equivalents or less, 6 equivalents or less, 5 equivalents or less, 4 equivalents or less, 3 equivalents or less, or 2 equivalents or less, relative to the thermally regenerable anhydride. Any two of the foregoing endpoints can be used to define a close-ended range, or a single endpoint can be used to define an open-ended range. For example, the organic mono-acid can be used in a range of 1-30 equivalents, 1-20 equivalents, 1-5 equivalents, 5-10 equivalents, 4-8 equivalents, or 10-20 equivalents relative to the thermally regenerable anhydride in the transanhydridization reaction.

In any of the processes described herein, including an integrated process and an anhydride production system, the separating steps are performed by any suitable method, including methods known in the art and described herein (e.g., reactive distillation, azeotropic distillation, extraction, extractive distillation, reactive extraction, mixing-settling, pervaporation, membrane separation, evaporation, condensation, flashing, fractionation, electrotreatment, flotation, phase separation, coalescence, hydrocycloning, decanting, parametric pumping, sublimation, ion exchange, adsorption, absorption, and/or crystallization).

In general, the separating step will provide a stream that comprises a majority (e.g., at least 50%) of the organic mono-acid. In some embodiments, the organic mono-acid stream comprises 60% or more (e.g., 65% or more, 70% or more, 75% or more, 80% or more, 85% or more, 90% or more, 95% or more, or 98% or more) of the organic mono-acid (e.g., acetic acid).

As described above with respect to the transanhydridization reaction, the transanhydridization process with respect to the integrated process or anhydride production system can include a regenerable anhydride that is cyclic or can form a cyclic structure. Suitable regenerable anhydrides includes a carboxylic acid anhydride, a sulfonic acid anhydride, a phosphinic acid anhydride, a phosphonic acid anhydride, and a mixed anhydride containing a combination of different acid moieties or different backbone structures. In some aspects, the regenerable anhydride is selected from succinic anhydride, glutaric anhydride, nitrophthalic anhydride, homophthalic anhydride, 1,2-ethane disulfonic acid, polyphosphoric acid, and ortho-sulfobenzoic anhydride. Preferably, the regenerable anhydride is glutaric anhydride.

The transanhydridization reaction in the integrated process can comprises a catalyst, if desired. Alternatively, or in addition, the heating step to regenerate the thermally regenerable anhydride can further comprise a catalyst and/or a solvent. Suitable catalysts and solvents are as described.

In any of the processes described herein, including an integrated process and an anhydride production system, the transanhydridization reaction is performed using any appropriate vessel or a series of vessels, including a continuous stirred tank reactor (CSTR), a batch reactor, a semibatch reactor, a plug flow reactor (PFR), and a catalytic reactor. Preferably, the transanhydridization vessel is a CSTR or a PFR. The effluent of the transanhydrization vessel can be directly coupled to one or more separation vessels, such as a flash, stripper, absorber, and/or distillation column. In a particular embodiment, the transanhydridization reaction is performed using a PFR followed by a flash.

In any of the processes described herein, including an integrated process and an anhydride production system, the intrinsic capital intensity of the process in 2020 USD is less than $5,000 (e.g., less than $4,500, less than $4,000, less than $3,500, less than $3,000, less than $2,500, less than $2,000, less than $1,500, or less than $1,000) per ton of installed annual capacity. In some embodiments, the intrinsic capital intensity of the process in 2020 USD is $1,000 or more (e.g., $1,000 or more, $1,500 or more, $2,000 or more, $2,500 or more, $3,000 or more, $3,500 or more, $4,000 or more, or $4,500 or more) per ton of installed annual capacity. Any two of the foregoing endpoints can be used to define a close-ended range, or a single endpoint can be used to define an open-ended range. The installed annual capacity is for a plant size with a capacity of less than 36 thousand metric tons per year (kmta) (e.g., less than 34 kmta, less than 30 kmta, less than 30 kmta, less than 28 kmta, less than 25 kmta, less than 22 kmta, less than 20 kmta, less than 18 kmta, less than 16 kmta, less than 15 kmta, less than 14 kmta, less than 12 kmta, less than 10 kmta, less than 8 kmta, less than 6 kmta, or less than 5 kmta).

In any of the methods described herein, the intrinsic capital intensity of the overall process is more than 5% lower than the intrinsic capital intensity of a ketene-based acetic acid to acetic anhydride process at the same plant size. For example, the intrinsic capital intensity of the overall process preferably is more than 10% lower (e.g., more than 15% lower, more than 20% lower, more than 25% lower, more than 30% lower, more than 35% lower, more than 40% lower) than the intrinsic capital intensity of a ketene-based acetic acid to acetic anhydride process at the same plant size. In any of these embodiments, the plant size is less than 50 kmta capacity (e.g., less than 45 kmta capacity, less than 40 kmta capacity, less than 35 kmta capacity, less than 30 kmta capacity, less than 25 kmta capacity, less than 20 kmta capacity, less than 15 kmta capacity, less than 10 kmta capacity, or less than 5 kmta capacity).

In any of the methods described herein, the intrinsic capital intensity of the ISBL (inside battery limits) equipment of the overall process is more than 5% lower than the intrinsic capital intensity of the ISBL equipment of a ketene-based acetic acid to acetic anhydride process at the same plant size. For example, the intrinsic capital intensity of the ISBL equipment of the overall process preferably is more than 10% lower (e.g., more than 15% lower, more than 20% lower, more than 25% lower, more than 30% lower, more than 35% lower, more than 40% lower) than the intrinsic capital intensity of the ISBL equipment of a ketene-based acetic acid to acetic anhydride process at the same plant size. In any of these embodiments, the plant size is less than 50 kmta capacity (e.g., less than 45 kmta capacity, less than 40 kmta capacity, less than 35 kmta capacity, less than 30 kmta capacity, less than 25 kmta capacity, less than 20 kmta capacity, less than 15 kmta capacity, less than 10 kmta capacity, or less than 5 kmta capacity).

In any of the methods described herein, the intrinsic capital intensity of the ISBL (inside battery limits) and OSBL (outside battery limits) equipment of the overall process is more than 5% lower than the intrinsic capital intensity of the ISBL and OSBL equipment of a ketene-based acetic acid to acetic anhydride process at the same plant size. For example, the intrinsic capital intensity of the ISBL and OSBL equipment of the overall process preferably is more than 10% lower (e.g., more than 15% lower, more than 20% lower, more than 25% lower, more than 30% lower, more than 35% lower, more than 40% lower) than the intrinsic capital intensity of the ISBL and OSBL equipment of a ketene-based acetic acid to acetic anhydride process at the same plant size. In any of these embodiments, the plant size is less than 50 kmta capacity (e.g., less than 45 kmta capacity, less than 40 kmta capacity, less than 35 kmta capacity, less than 30 kmta capacity, less than 25 kmta capacity, less than 20 kmta capacity, less than 15 kmta capacity, less than 10 kmta capacity, or less than 5 kmta capacity).

As used herein, the term "intrinsic capital intensity" refers to the capital cost in dollars, divided by installed annual capacity of a chemical plant performing a specific process or chemical transformation. The intrinsic capital intensity for a process can be defined as that of the ISBL (inside battery limits) equipment or the ISBL plus OSBL (outside battery limits) equipment (either on an installed cost basis), or the entire plant project cost.

The invention is further illustrated by the following aspects.

Aspect 1. A first process of producing an anhydride of an organic mono-acid comprising performing a transanhydridization reaction of an organic mono-acid and a thermally regenerable anhydride to produce the anhydride of the organic mono-acid and an acid of the thermally regenerable anhydride, wherein at least one of the organic mono-acid and thermally regenerable anhydride is provided by a preprocess that is integrated with the first process.

Aspect 2. The process of aspect 1, comprising providing a preprocess comprising reacting the anhydride of the organic mono-acid with a feedstock to produce a desired product and an organic mono-acid by-product stream;

separating the desired product and organic mono-acid by-product stream;

using the separated organic mono-acid by-product stream in the transanhydridization reaction to produce the anhydride of the organic mono-acid and the acid of the thermally regenerable anhydride;

separating the anhydride of the organic mono-acid and the acid of the thermally regenerable anhydride;

recycling the anhydride of the organic mono-acid to the preprocess;

heating the acid of the thermally regenerable anhydride to produce thermally regenerable anhydride; and recycling the regenerated thermally regenerable anhydride for the transanhydridization.

Aspect 3. The process of aspect 1 or 2, wherein the preprocess is a cellulose ester process, an acetylated wood process, a tetraacetylethylenediamine production process, an aspirin production process, an anhydride production process, a polymer production process, or a petrochemical production process.

Aspect 4. The process of aspect 3, wherein the anhydride production preprocess is a ketene process or carbonylation process to produce acetic anhydride.

Aspect 5. The process of any one of aspects 2-4, wherein the organic mono-acid by-product stream comprises a carboxylic acid, a sulfonic acid, a sulfinic acid, a phosphonic acid, or a phosphinic acid.

Aspect 6. The process of aspect 5, wherein the carboxylic acid is a $C_{1-18}$ monocarboxylic acid.

Aspect 7. The process of aspect 6, wherein the $C_{1-18}$ monocarboxylic acid is selected from formic acid, acetic acid, propionic acid, butanoic acid (butyric acid), isobutyric acid, pentanoic acid (valeric acid), hexanoic acid (caproic acid), heptanoic acid, octanoic acid (caprylic acid), decanoic acid (capric acid), and dodecanoic acid.

Aspect 8. The process of any one of aspects 1-5, wherein the organic mono-acid is acetic acid, propionic acid, butanoic acid (butyric acid), isobutyric acid, triflic acid, trifluoroacetic acid, maleic acid, or a combination thereof.

Aspect 9. The process of aspect 8, wherein the organic mono-acid is acetic acid.

Aspect 10. The process of aspect 1, comprising providing a preprocess that produces a desired product and a $C_{1-4}$ organic mono-acid by-product stream;

separating the desired product and the $C_{1-4}$ organic mono-acid by-product stream;

using the separated $C_{1-4}$ organic mono-acid by-product stream and glutaric anhydride in the transanhydridization reaction to produce the anhydride of the $C_{1-4}$ organic mono-acid and glutaric acid;

separating the anhydride of the $C_{1-4}$ organic mono-acid and the glutaric acid;

recycling the anhydride of the $C_{1-4}$ organic mono-acid to the preprocess as a reagent;

heating the glutaric acid to produce regenerated glutaric anhydride; and recycling the regenerated glutaric anhydride for the transanhydridization.

Aspect 11. The process of aspect 10, wherein the preprocess is a cellulose ester process, a polymer production process, or a petrochemical production process.

Aspect 12. The process of aspect 10 or 11, wherein the $C_{1-4}$ organic mono-acid by-product stream comprises acetic acid, propionic acid, n-butyric acid, i-butyric acid, or a mixture thereof.

Aspect 13. The process of aspect 1, comprising providing a preprocess that produces a cellulose ester product and a $C_{1-4}$ organic mono-acid by-product stream;

separating the cellulose ester product and the $C_{1-4}$ organic mono-acid by-product stream;

using the separated $C_{1-4}$ organic mono-acid by-product stream and glutaric anhydride in the transanhydridization reaction to produce the anhydride of the $C_{1-4}$ organic mono-acid and glutaric acid;

separating the anhydride of the $C_{1-4}$ organic mono-acid and the glutaric acid;

recycling the anhydride of the $C_{1-4}$ organic mono-acid to the preprocess as a reagent;

heating the glutaric acid to produce regenerated glutaric anhydride; and recycling the regenerated glutaric anhydride for the transanhydridization.

Aspect 14. The process of aspect 13, wherein the $C_{1-4}$ organic mono-acid by-product stream is a $C_{2-4}$ organic mono-acid by-product stream.

Aspect 15. The process of aspect 13 or 14, wherein the $C_{1-4}$ organic mono-acid by-product stream comprises acetic acid, propionic acid, n-butyric acid, i-butyric acid, or a mixture thereof.

Aspect 16. The process of any one of aspects 13-15, wherein the $C_{1-4}$ organic mono-acid by-product stream further comprises the anhydride of the $C_{1-4}$ organic mono-acid and a mineral acid.

Aspect 17. The process of aspect 16, wherein the mineral acid comprises sulfuric acid.

Aspect 18. The process of any one of aspects 4-8, wherein a stream comprising the anhydride of the $C_{1-4}$ organic mono-acid further comprises unreacted $C_{1-4}$ organic mono-acid.

Aspect 19. The process of aspect 1, comprising providing a preprocess using acetic anhydride to produce an acetylated wood product and an acetic acid by-product stream;

separating the acetylated wood product and the acetic acid by-product stream;

using the separated acetic acid by-product stream and glutaric anhydride in the transanhydridization reaction to produce acetic anhydride and glutaric acid;

separating the acetic anhydride and glutaric acid;

recycling the acetic anhydride to the preprocess as a reagent;

heating the glutaric acid to produce regenerated glutaric anhydride; and recycling the regenerated glutaric anhydride for the transanhydridization.

Aspect 20. The process of aspect 19, wherein the separated acetic acid by-product stream further comprises at least one additional component selected from acetic anhydride, a terpene, a chloride-containing compound, and a mineral acid.

Aspect 21. The process of aspect 20, wherein the separated acetic acid by-product stream further comprises at least one terpene.

Aspect 22. The process of any one of aspects 20 or 21, wherein the separated acetic acid by-product stream further comprises at least one chloride-containing compound.

Aspect 23. The process of aspect 21 or 22, wherein the at least one terpene and/or the at least one chloride-containing compound is at least partially removed from the separated acetic acid by-product stream prior to the transanhydridization reaction.

Aspect 24. The process of aspect 23, wherein the at least one terpene and/or the at least one chloride-containing compound is at least partially removed by azeotropic distillation or passing the separated acetic acid by-product stream through an activated carbon bend.

Aspect 25. The process of aspect 1, comprising providing a preprocess using acetic anhydride to produce a tetraacetylethylenediamine (TAED) product and an acetic acid by-product stream;

separating the tetraacetylethylenediamine product and the acetic acid by-product stream;

using the separated acetic acid by-product stream and glutaric anhydride in the transanhydridization reaction to produce acetic anhydride and glutaric acid;

separating the acetic anhydride and glutaric acid;

recycling the acetic anhydride to the preprocess as a reagent;

heating the glutaric acid to produce regenerated glutaric anhydride; and recycling the regenerated glutaric anhydride for the transanhydridization.

Aspect 26. The process of aspect 25, wherein the acetic acid by-product stream further comprises acetic anhydride.

Aspect 27. The process of aspect 25 or 26, wherein unreacted acetic acid from the transanhydridization reaction is separated and routed back to the transanhydridization reaction, a diacetylethylenediamine (DAED) reactor, or both.

Aspect 28. The process of aspect 1, comprising providing a ketene preprocess that produces acetic anhydride and excess acetic acid reagent;

separating the acetic anhydride and the excess acetic acid reagent into streams;

using the separated excess acetic acid reagent stream and glutaric anhydride in the transanhydridization reaction to produce acetic anhydride and glutaric acid;

separating the acetic anhydride and glutaric acid;

combining the acetic anhydride produced from the transanhydridization with the acetic anhydride produced in the ketene preprocess;

heating the glutaric acid to produce regenerated glutaric anhydride; and recycling the regenerated glutaric anhydride for the transanhydridization.

Aspect 29. The process of aspect 28, further comprising recycling unreacted acetic acid from the transanhydridization reaction back to the transanhydridization reaction, to the ketene preprocess, or both.

Aspect 30. The process of aspect 1, comprising providing a ketene preprocess that produces acetic anhydride and excess acetic acid reagent;

separating the acetic anhydride and the excess acetic acid reagent into streams;

using the separated acetic acid by-product stream and glutaric anhydride in the transanhydridization reaction to produce acetic anhydride and glutaric acid;

separating the acetic anhydride and glutaric acid;

using the acetic anhydride in a third anhydride production process for producing $C_{3-4}$ anhydride;

heating the glutaric acid to produce regenerated glutaric anhydride; and recycling the regenerated glutaric anhydride for the transanhydridization.

Aspect 31. The process of aspect 30, further comprising reacting the acetic anhydride from the transanhydridization reaction with $C_{3-4}$ organic mono-acid to produce the corresponding anhydride and acetic acid in the third anhydride production process; and recycling the acetic acid produced in the third anhydride production process back to the ketene preprocess and/or the transanhydridization reaction.

Aspect 32. The process of aspect 1, comprising providing a carbonylation preprocess that produces acetic anhydride and an acetic acid by-product;

separating the acetic anhydride and the acetic acid by-product into streams;

using the separated acetic acid by-product stream and glutaric anhydride in the transanhydridization reaction to produce acetic anhydride and glutaric acid;

separating the acetic anhydride and glutaric acid;

combining the acetic anhydride produced from the transanhydridization with the acetic anhydride produced in the carbonylation preprocess;

heating the glutaric acid to produce regenerated glutaric anhydride; and recycling the regenerated glutaric anhydride for the transanhydridization.

Aspect 33. The process of aspect 32, further comprising recycling unreacted acetic acid back to the transanhydridization reaction.

Aspect 34. The process of aspect 1, comprising providing a vinyl acetate monomer preprocess that produces vinyl acetate and excess acetic acid reagent;

separating the vinyl acetate monomer and the excess acetic acid reagent into streams;

using the separated excess acetic acid reagent stream and glutaric anhydride in the transanhydridization reaction to produce acetic anhydride and glutaric acid;

separating the acetic anhydride and glutaric acid;

heating the glutaric acid to produce regenerated glutaric anhydride; and recycling the regenerated glutaric anhydride for the transanhydridization.

Aspect 35. The process of aspect 34, wherein methyl acetate produced as a co-product in the vinyl acetate monomer preprocess is hydrolyzed to provide acetic acid.

Aspect 36. The process of aspect 35, wherein the acetic acid produced from methyl acetate is used as a reagent in the transanhydridization reaction.

Aspect 37. The process of any one of aspects 1-36, wherein 1-20 equivalents of the organic mono-acid is used in the transanhydridization.

Aspect 38. The process of any one of aspects 2-37, wherein the separating step is by distillation.

Aspect 39. The process of any one of aspects 1-38, wherein the transanhydridization reaction is performed using reactive distillation.

Aspect 40. The process of any one of aspects 1-38, wherein the transanhydridization reaction is performed using a continuous stirred tank reactor (CSTR).

Aspect 41. The process of any one of aspects 2-40, wherein an organic mono-acid stream comprises at least 60% of the organic mono-acid.

Aspect 42. The process of any one of aspects 1-41, wherein the regenerable anhydride is cyclic or can form a cyclic structure.

Aspect 43. The process of any one of aspects 1-42, wherein the regenerable anhydride is selected from a carboxylic acid anhydride, a sulfonic acid anhydride, a phosphinic acid anhydride, a phosphonic acid anhydride, and a mixed anhydride containing a combination of different acid moieties or different backbone structures.

Aspect 44. The process of any one of aspects 1-43, wherein the regenerable anhydride is selected from succinic anhydride, glutaric anhydride, nitrophthalic anhydride, homophthalic anhydride, 1,2-ethane disulfonic acid, polyphosphoric acid, ortho-sulfobenzoic anhydride, and mixed benzoic acid-trifluoroacetic acid anhydride.

Aspect 45. The process of any one of aspects 1-44, wherein the regenerable anhydride is glutaric anhydride.

Aspect 46. The process of any one of aspects 1-45, wherein the transanhydridization reaction comprises a catalyst.

Aspect 47. The process of any one of aspects 2-46, wherein the heating step to regenerate the thermally regenerable anhydride further comprises a catalyst and/or a solvent.

Aspect 48. An anhydride production system comprising a transanhydridization vessel for receiving an organic mono-acid and a thermally regenerable anhydride that is in fluid communication with (a) a first fluid channel for conveying the organic mono-acid and (b) a second fluid channel for conveying the thermally regenerable anhydride;

a third fluid channel for conveying an anhydride of the organic mono-acid and an acid of the thermally regenerable anhydride to a first separation vessel, a fourth fluid channel for conveying separated anhydride of the organic mono-acid from the first separation vessel to a first anhydride vessel;

a fifth fluid channel for conveying separated acid of the thermally regenerated anhydride from the first separation vessel to a regeneration vessel;

wherein the first anhydride vessel is in fluid communication with an integrated system for reacting the separated anhydride of the organic mono-acid;

a second anhydride vessel for receiving fresh anhydride of the organic mono-acid in the integrated system is in fluid communication with the first fluid channel; and the regeneration vessel is in fluid communication with the second fluid channel.

Aspect 49. The anhydride production system of aspect 48, wherein the second anhydride vessel is in fluid communication with a reaction vessel, the reaction vessel is in fluid communication with (a) a sixth fluid channel for conveying feedstock and (b) a second separation vessel, the second separation vessel is in fluid communication with the first fluid channel, and the first anhydride vessel is in fluid communication with the second anhydride vessel or the reaction vessel.

Aspect 50. The anhydride production system of aspect 49, wherein the second separation vessel comprises a seventh fluid channel for conveying a desired product other than the organic mono-acid to a collection vessel.

Aspect 51. The anhydride production system of aspect 50, wherein the desired product other than the organic mono-acid is a cellulose ester product.

Aspect 52. The anhydride production system of aspect 50, wherein the desired product other than the organic mono-acid is an acetylated wood product.

Aspect 53. The anhydride production system of aspect 50, wherein the desired product other than the organic mono-acid is a tetraacetylethylenediamine product.

Aspect 54. An anhydride production system comprising a transanhydridization vessel for receiving an organic mono-acid by-product from an integrated preprocess and a thermally regenerable anhydride that is in fluid communication with (a) a first fluid channel for conveying the organic mono-acid by-product that is in fluid communication with the preprocess and (b) a second fluid channel for conveying the thermally regenerable anhydride;

a third fluid channel for conveying an anhydride of the organic mono-acid by-product and an acid of the thermally regenerable anhydride to a first separation vessel, a fourth fluid channel for conveying separated anhydride of the organic mono-acid by-product from the first separation vessel to a first anhydride vessel;

a fifth fluid channel for conveying separated acid of the thermally regenerated anhydride from the first separation vessel to a regeneration vessel;

wherein the regeneration vessel is in fluid communication with the second fluid channel.

Aspect 55. The anhydride production system of aspect 54, wherein the first anhydride vessel is in fluid communication with an integrated system that produces the anhydride of the organic mono-acid and the organic mono-acid by-product.

Aspect 56. The anhydride production system of aspect 55, further comprising a second anhydride vessel for receiving anhydride of the organic mono-acid that is produced in the integrated system and that is in fluid communication with a second separation vessel, wherein the second separation vessel is in fluid communication with (a) a reaction vessel for receiving a mixture of the anhydride of the organic mono-acid and the organic mono-acid by-product and (b) the first fluid channel.

Aspect 57. The anhydride production system of aspect 54, wherein the organic mono-acid by-product from an integrated preprocess is acetic acid;

the integrated preprocess is a ketene process;

the thermally regenerable anhydride is glutaric anhydride; and the anhydride of the organic mono-acid by-product is acetic anhydride.

Aspect 58. The anhydride production system of aspect 57, wherein the first anhydride vessel is in fluid communication with a third anhydride production process that produces $C_{3-4}$ anhydride.

Aspect 59. The anhydride production system of aspect 58, further comprising a third anhydride production process vessel for receiving a mixture of acetic anhydride produced in the transanhydridization reaction and a $C_{3-4}$ organic mono-acid that is in fluid communication with a third separation vessel, wherein the third separation vessel is in fluid communication with (a) a third anhydride vessel for receiving the anhydride of the $C_{3-4}$ organic mono-acid; and (b) the first fluid channel, the ketene preprocess, or both.

Aspect 60. The anhydride production system of aspect 59, wherein the second anhydride vessel is in fluid communication with the third anhydride production process vessel.

Aspect 61. The anhydride production system of any one of aspects 48-56, wherein the organic mono-acid by-product comprises a carboxylic acid, a sulfonic acid, a sulfinic acid, a phosphonic acid, or a phosphinic acid.

Aspect 62. The anhydride production system of aspect 61, wherein the carboxylic acid is a $C_{1-18}$ monocarboxylic acid.

Aspect 63. The anhydride production system of aspect 62, wherein the $C_{1-18}$ monocarboxylic acid is selected from formic acid, acetic acid, propionic acid, butanoic acid, isobutyric acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, and a combination thereof.

Aspect 64. The anhydride production system of any one of aspects 61-63, wherein the organic mono-acid by-product is acetic acid.

Aspect 65. The anhydride production system of any one of aspects 48-56 and 61-64, wherein the regenerable anhydride is cyclic or can form a cyclic structure.

Aspect 66. The anhydride production system of any one of aspects 48-56 and 61-65, wherein the regenerable anhydride is selected from a carboxylic acid anhydride, a sulfonic acid anhydride, a phosphinic acid anhydride, a phosphonic acid anhydride, and a mixed anhydride containing a combination of different acid moieties or different backbone structures.

Aspect 67. The anhydride production system of any one of aspects 48-56 and 61-66, wherein the regenerable anhydride is selected from succinic anhydride, glutaric anhydride, nitrophthalic anhydride, homophthalic anhydride, 1,2-ethane disulfonic acid, polyphosphoric acid, ortho-sulfobenzoic anhydride, and mixed benzoic acid-trifluoroacetic acid anhydride.

Aspect 68. The anhydride production system of any one of aspects 48-56 and 61-67, wherein the regenerable anhydride is glutaric anhydride.

Aspect 69. A process comprising a wood acetylation process coupled to an acetic anhydride production process, wherein the wood acetylation process comprises subjecting wood to acetylation comprising an acetylation fluid, and the acetic anhydride production process comprises performing a transanhydridization reaction between acetic acid and a thermally regenerable anhydride to produce an acetic anhydride reaction fluid comprising acetic anhydride and acetic acid, wherein the raw anhydride reaction fluid is used in the wood acetylation process as an acetylation fluid.

Aspect 70. The process of aspect 69, further comprising recovering acetylation fluid from the wood acetylation process to obtain recovered acetylation fluid comprising acetic acid and acetic anhydride; and distilling the recovered acetylation fluid to obtain acetic acid by-product, wherein the acetic acid by-product is used as a reactant in the transanhydridization reaction.

Aspect 71. The process of aspect 70, wherein the acetic acid by-product comprises at least 60% acetic acid.

Aspect 72. The process of any one of aspects 69-71, wherein 1-20 equivalents of the organic mono-acid is used in the transanhydridization reaction.

Aspect 73. The process of any one of aspects 69-72, wherein the transanhydridization reaction is performed using reactive distillation.

Aspect 74. An integrated wood acetylation and anhydride production system comprising a wood acetylation vessel for receiving wood and an acetylation fluid that is in fluid communication with a first fluid channel for conveying recovered acetylation fluid;

a first separation vessel for receiving the recovered acetylation fluid from the first fluid channel and that is in fluid communication with a recovered acetic anhydride vessel and an acetic acid by-product vessel;

a transanhydridization vessel for receiving acetic acid by-product and a thermally regenerable anhydride that is in fluid communication with (a) the acetic acid by-product vessel; and (b) a second fluid channel for conveying the thermally regenerable anhydride;

a third fluid channel for conveying acetic anhydride and an acid of the thermally regenerable anhydride to a second separation vessel;

a fourth fluid channel for conveying separated acetic anhydride from the second separation vessel to a first anhydride vessel;

a fifth fluid channel for conveying separated acid of the thermally regenerated anhydride from the first separation vessel to a regeneration vessel;

wherein the first anhydride vessel is in fluid communication with the wood acetylation vessel; and the regeneration vessel is in fluid communication with the second fluid channel.

Aspect 75. A process of supplying an acetic acid reactant feed to a transanhydridization reaction unit, wherein the acetic acid reactant feed is acetylation fluid that has been directly recovered from a wood acetylation process and which comprises acetic acid and acetic anhydride.

Aspect 76. The process of aspect 75, wherein the transanhydridization reaction unit produces acetic anhydride from acetic acid from the acetic acid reactant feed and a thermally regenerable anhydride.

Aspect 77. The process of aspect 75 or 76, wherein the acetic acid reactant feed comprises at least 25% acetic acid.

Aspect 78. The process of aspect 77, wherein the acetic acid reactant feed comprises at least 20 ppm of terpenes.

Aspect 79. The process of any one of aspects 1-47, 69-73, or 75-78, wherein the intrinsic capital intensity of the process in 2020 USD is less than $5,000 per ton of installed annual capacity at a plant size of less than 36 thousand metric tons per year capacity.

The following examples further illustrate the invention but, of course, should not be construed as in any way limiting its scope.

Example 1

This example demonstrates a general method of producing an anhydride of an organic mono-acid by reacting an organic mono-acid and a regenerable anhydride.

A low-boiling monocarboxylic acid (such as acetic acid, propionic acid, or isobutyric acid) is fed to a reactor and reacted with a higher-boiling regenerable cyclic anhydride (such as succinic anhydride, glutaric anhydride, 1,2-ethane-disulfonic acid anhydride, or ortho-sulfobenzoic anhydride) to generate the anhydride of the monocarboxylic acid and the diacid form of the regenerable cyclic anhydride.

The mixture of products and starting material is separated in a series of flash stages or distillations to yield a first stream principally comprised of the generated anhydride and residual monocarboxylic acid and a second stream principally comprised of the residual regenerable cyclic anhydride and the generated diacid of the regenerable cyclic anhydride. The stream containing the anhydride product is then further concentrated in the anhydride product through partial condensation, flash, or distillation, and most of the residual monocarboxylic acid is recycled to the initial reactor. The stream containing residual regenerable cyclic anhydride is regenerated thermally, generated water is removed, and the regenerable cyclic anhydride is recycled to the reactor. FIG.

Figure 12:
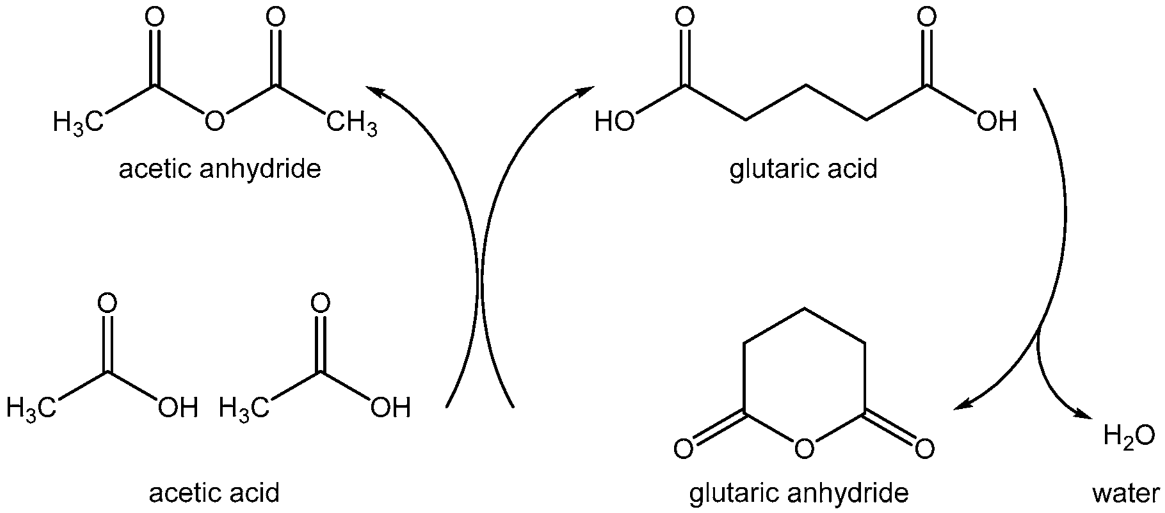
FIG. 12 is a reaction scheme illustrating acetic acid (organic mono-acid) reacting with glutaric anhydride (regenerable anhydride) to form acetic anhydride (anhydride of the organic mono-acid) and glutaric acid (diacid of the anhydride), which is subsequently dehydrated to reform glutaric anhydride (regenerable anhydride).

11 is a scheme illustrating an acetic acid feed (AcOH) feed and a glutaric anhydride feed to generate acetic anhydride ($Ac_2O$). FIG. 12 shows the reaction scheme for this process. Acetic acid (organic mono-acid) is reacted with glutaric anhydride (regenerable anhydride) to form acetic anhydride (anhydride of the organic mono-acid) and glutaric acid (diacid of the regenerable anhydride). The glutaric acid is dehydrated to regenerate the glutaric anhydride (regenerable anhydride).

Example 2

This example demonstrates a method of producing various anhydrides using a regenerable anhydride and an organic mono-acid in an embodiment of the invention.

Following the procedure set forth in Example 1, solutions of regenerable anhydride in organic mono-acid were heated at either 50° C. or 100° C. for the indicated time in a batch reactor. No solvents or catalysts were used. The products were analyzed by nuclear magnetic resonance (NMR) spectra. No byproducts were detected by NMR, suggesting very high selectivity. The results of these experiments are set forth in Table 1.

TABLE 1

| Organic mono-acid (concentration (M)) | Regenerable Anhydride (concentration (M)) | Temperature (° C.) | Time (hr) | Acid Conversion (mol %) |
|---|---|---|---|---|
| Acetic Acid (16.0) | Glutaric Anhydride (1.0) | 50 | 0.5 | 2.8 |
| Acetic Acid (14.4) | Glutaric Anhydride (2.0) | 50 | 0.5 | 4.3 |
| Acetic Acid (11.3) | Glutaric Anhydride (4.0) | 50 | 0.5 | 6.7 |
| Acetic Acid (9.9) | Glutaric Anhydride (5.0) | 100 | 0.25 | 8.0 |
| Acetic Acid (9.9) | Glutaric Anhydride (5.0) | 100 | 0.5 | 12.6 |
| Acetic Acid (9.1) | Polyphosphoric Acid* (4.5) | 100 | 0.5 | 9.1 |

TABLE 1-continued

| Organic mono-acid (concentration (M)) | Regenerable Anhydride (concentration (M)) | Temperature (° C.) | Time (hr) | Acid Conversion (mol %) |
|---|---|---|---|---|
| Acetic Acid (14.9) | o-Sulfobenzoic Acid Anhydride (1) | 100 | 0.5 | 1.8 |
| Acetic Acid (7.8) | o-Sulfobenzoic Acid Anhydride (2) | 100 | 0.5 | 5.2 |
| Acetic Acid (7.8) | o-Sulfobenzoic Acid Anhydride (4.8) | 100 | 0.5 | 8.0 |
| Propanoic Acid (7.6) | Glutaric Anhydride (4.9) | 100 | 0.5 | 10.1 |

*Molarity based on c.a. 84 wt % $P_2O_5$ equivalent as anhydride equivalent, balance $H_3PO_4$.

Example 3

This example demonstrates a method of producing various anhydrides using a regenerable anhydride and an organic mono-acid under various reaction conditions in an embodiment of the invention.

The solids and/or liquids were added to 2-dram vials with polytetrafluoroethylene (PTFE) caps or 2-5 ml microwave vials with crimp caps, and each vial was equipped with a stir bar. In some trials, a corresponding co-solvent was added to the corresponding vial and sealed. The sealed vials were placed into a preheated (75-150° C.) aluminum pie block, and the reactions were stirred at 800 rpm for 1 hr. The vials were removed from the heat and cooled on a room temperature aluminum pie block. If the reaction mixture was homogeneous at room temperature, a dichloromethane (DCM) standard was added, and an NMR sample was prepared. If the reaction mixture was a solid at room temperature, an appropriate amount of DMSO or DMF was added to the reaction mixture to dissolve the solids. A DCM standard was added to the reaction mixture and an NMR sample was prepared. The solutions were added to NMR tubes containing a capillary containing $C_6D_6$ and NMRs were taken with long relaxation delays to ensure quantitative NMRs. The reaction conditions are set forth in Table 2, and the products are set forth in Table 3.

TABLE 2

| Entry | T (° C.) | Acid (HX) | Anhydride ($X_2$'O) | Co-solvent (CS) | [CS] (M) | [HX] (M) | [$X_2$'O] (M) |
|---|---|---|---|---|---|---|---|
| 1 | 75 | Acetic | Glutaric | N/A | N/A | 8.75 | 4.38 |
| 2 | 75 | Propionic | Glutaric | N/A | N/A | 8.75 | 4.38 |
| 3 | 75 | Chloroacetic | Glutaric | N/A | N/A | 7.87 | 3.94 |
| 4 | 110 | Acetic | Glutaric | N/A | N/A | 8.75 | 4.38 |
| 5 | 110 | Propionic | Glutaric | N/A | N/A | 8.75 | 4.38 |
| 6 | 110 | Chloroacetic | Glutaric | N/A | N/A | 7.87 | 3.94 |
| 7 | 110 | Benzoic | Glutaric | N/A | N/A | 6.30 | 3.15 |
| 8 | 110 | Cinnamic | Glutaric | N/A | N/A | 5.25 | 2.63 |
| 9 | 150 | Acetic | Glutaric | N/A | N/A | 8.75 | 4.38 |
| 10 | 150 | Propionic | Glutaric | N/A | N/A | 8.75 | 4.38 |
| 11 | 150 | Chloroacetic | Glutaric | N/A | N/A | 7.87 | 3.94 |
| 12 | 150 | Benzoic | Glutaric | N/A | N/A | 6.30 | 3.15 |
| 13 | 150 | Cinnamic | Glutaric | N/A | N/A | 5.25 | 2.63 |
| 14 | 110 | Acetic | Succinic | N/A | N/A | 8.75 | 4.38 |
| 15 | 150 | Acetic | Succinic | N/A | N/A | 8.75 | 4.38 |
| 16 | 150 | Acetic | Pyromellitic | N/A | N/A | 8.75 | 2.19 |
| 17 | 150 | Acetic | Glutaric | Cyclohexanone | 4.82 | 4.38 | 2.19 |
| 18 | 150 | Acetic | Glutaric | Cyclohexanone | 6.43 | 2.92 | 1.46 |
| 19 | 150 | Acetic | Glutaric | Cyclohexanone | 7.72 | 1.75 | 0.88 |
| 20 | 150 | Acetic | Glutaric | m-xylene | 4.09 | 4.38 | 2.19 |
| 21 | 150 | Acetic | Glutaric | m-xylene | 5.45 | 2.92 | 1.46 |
| 22 | 150 | Acetic | Glutaric | m-xylene | 6.54 | 1.75 | 0.88 |
| 23 | 150 | Myristic | Glutaric | DMF | 6.46 | 2.13 | 1.06 |

TABLE 2-continued

| Entry | T (° C.) | Acid (HX) | Anhydride ($X_2$'O) | Co-solvent (CS) | [CS] (M) | [HX] (M) | [$X_2$'O] (M) |
|---|---|---|---|---|---|---|---|
| 24 | 150 | Benzoic | Glutaric | DMF | 6.46 | 3.15 | 1.58 |
| 25 | 150 | Cinnamic | Glutaric | DMF | 6.46 | 3.15 | 1.58 |
| 26 | 75 | Acetic | Sulfobenzoic | N/A | N/A | 8.75 | 4.38 |
| 27 | 110 | Acetic | Sulfobenzoic | N/A | N/A | 8.75 | 4.38 |
| 28 | 150 | Acetic | Sulfobenzoic | N/A | N/A | 8.75 | 4.38 |
| 29 | 110 | Myristic | Glutaric | N/A | N/A | 4.25 | 2.13 |
| 30 | 110 | Trifluoroacetic | Glutaric | N/A | N/A | 10.00 | 5.00 |
| 31 | 110 | Methanesulfonic | Glutaric | N/A | N/A | 9.63 | 4.81 |
| 32 | 110 | Acetic | Propane phosphonic | N/A | N/A | 8.75 | 1.46 |
| 33 | 75 | Trifluoroacetic | Glutaric | N/A | N/A | 10.00 | 5.00 |
| 34 | 75 | Methanesulfonic | Glutaric | N/A | N/A | 9.63 | 4.81 |
| 35 | 75 | Acetic | Propane phosphonic | N/A | N/A | 8.75 | 1.46 |
| 36 | 110 | Trifluoroacetic | Glutaric | N/A | N/A | 5.00 | 5.00 |
| 37 | 110 | Trifluoroacetic | Glutaric | N/A | N/A | 10.00 | 2.50 |
| 38 | 110 | Methanesulfonic | Glutaric | N/A | N/A | 6.02 | 6.02 |
| 39 | 110 | Methanesulfonic | Glutaric | N/A | N/A | 11.00 | 2.75 |
| 40 | 110 | Acetic | Poly phosphoric | N/A | N/A | 13.11 | 2.19 |
| 41 | 110 | Acetic | Poly phosphoric | N/A | N/A | 13.99 | 1.75 |
| 42 | 75 | Trifluoroacetic | Glutaric | N/A | N/A | 10.00 | 5.00 |
| 43 | 75 | Methanesulfonic | Glutaric | N/A | N/A | 9.63 | 4.81 |
| 44 | 75 | Acetic | Poly phosphoric | N/A | N/A | 13.13 | 2.19 |
| 45 | 75 | Acetic | Propane phosphonic | N/A | N/A | 13.13 | 0.73 |
| 46 | 75 | Myristic | Glutaric | N/A | N/A | 4.25 | 2.13 |
| 47 | 150 | Trifluoroacetic | Glutaric | N/A | N/A | 10.00 | 5.00 |
| 48 | 150 | Methanesulfonic | Glutaric | N/A | N/A | 9.63 | 4.81 |
| 49 | 150 | Acetic | Poly phosphoric | N/A | N/A | 13.13 | 2.19 |
| 50 | 150 | Myristic | Glutaric | N/A | N/A | 4.25 | 2.13 |
| 51 | 150 | Acetic | Glutaric | toluene | 4.09 | 4.38 | 2.19 |
| 52 | 150 | Acetic | Glutaric | toluene | 5.45 | 2.92 | 1.46 |
| 53 | 150 | Acetic | Glutaric | toluene | 6.54 | 1.75 | 0.88 |
| 54 | 150 | Myristic | Glutaric | toluene | 4.09 | 2.13 | 1.06 |
| 55 | 150 | Myristic | Glutaric | toluene | 5.45 | 1.42 | 0.71 |
| 56 | 150 | Benzoic | Glutaric | toluene | 4.09 | 3.15 | 1.58 |
| 57 | 150 | Benzoic | Glutaric | toluene | 5.45 | 2.10 | 1.05 |
| 58 | 150 | Benzoic | Glutaric | toluene | 6.54 | 1.26 | 0.63 |
| 59 | 150 | Myristic | Glutaric | Cyclohexanone | 4.82 | 2.13 | 1.06 |
| 60 | 150 | Myristic | Glutaric | Cyclohexanone | 6.43 | 1.42 | 0.71 |
| 61 | 150 | Benzoic | Glutaric | Cyclohexanone | 4.82 | 3.15 | 1.58 |
| 62 | 150 | Benzoic | Glutaric | Cyclohexanone | 6.43 | 2.10 | 1.05 |
| 63 | 150 | Benzoic | Glutaric | Cyclohexanone | 7.72 | 1.26 | 0.63 |

TABLE 3

| Entry | Anhydride of the Acid [$X_2$O] (M) | Acid of the Anhydride [HX'] (M) | Acid (HX) Conversion (mol %) | Anhydride ($X_2$'O) Conversion (mol %) |
|---|---|---|---|---|
| 1 | 0.11 | 0.31 | 2.6% | 7.0% |
| 2 | 0.18 | 0.38 | 4.0% | 8.7% |
| 3 | 0.01 | 0.37 | 0.2% | 9.3% |
| 4 | 0.26 | 0.39 | 5.9% | 9.0% |
| 5 | 0.37 | 0.56 | 8.6% | 12.7% |
| 6 | 0.02 | 0.38 | 0.5% | 9.7% |
| 7 | 0.13 | 0.40 | 4.2% | 12.6% |
| 8 | 0.03 | 0.31 | 1.0% | 11.6% |
| 9 | 0.44 | 0.73 | 10.0% | 16.7% |
| 10 | 0.36 | 0.54 | 8.3% | 12.3% |
| 11 | 0.02 | 0.41 | 0.6% | 10.4% |
| 12 | 0.12 | 0.49 | 3.9% | 15.7% |
| 13 | 0.09 | 0.35 | 3.2% | 13.4% |
| 14 | 0.04 | N/D | 0.9% | N/D |
| 15 | 0.07 | N/D | 1.6% | N/D |
| 16 | 0.02 | 0.10 | 0.2% | 4.7% |
| 17 | 0.08 | 0.20 | 3.6% | 9.0% |
| 18 | 0.04 | 0.15 | 3.0% | 10.0% |
| 19 | 0.01 | 0.10 | 1.7% | 11.1% |

TABLE 3-continued

| Entry | Anhydride of the Acid [$X_2$O] (M) | Acid of the Anhydride [HX'] (M) | Acid (HX) Conversion (mol %) | Anhydride ($X_2$'O) Conversion (mol %) |
|---|---|---|---|---|
| 20 | 0.17 | 0.37 | 7.8% | 16.7% |
| 21 | 0.10 | 0.25 | 6.9% | 16.8% |
| 22 | 0.05 | 0.17 | 5.8% | 19.5% |
| 23 | 0.06 | 0.07 | 5.8% | 11.9% |
| 24 | 0.03 | 0.18 | 2.0% | 11.6% |
| 25 | 0.01 | 0.14 | 0.7% | 9.0% |
| 26 | 1.37 | 2.21 | 31.3% | 50.5% |
| 27 | 1.58 | 2.68 | 36.2% | 61.2% |
| 28 | 1.65 | 2.88 | 37.7% | 65.9% |
| 29 | 0.15 | 0.30 | 7.2% | 14.3% |
| 30 | 0.03 | 0.29 | 0.5% | 5.8% |
| 31 | 0.02 | 0.66 | 0.3% | 13.6% |
| 32 | 0.52 | N/D | 11.9% | N/D |
| 33 | 0.03 | 0.31 | 0.5% | 6.2% |
| 34 | 0.03 | 0.68 | 0.5% | 14.2% |
| 35 | 0.55 | N/D | 12.5% | N/D |
| 36 | 0.02 | 0.27 | 0.6% | 5.4% |
| 37 | 0.03 | 0.18 | 0.5% | 7.3% |
| 38 | 0.01 | 0.58 | 0.5% | 9.7% |

TABLE 3-continued

| Entry | Anhydride of the Acid $[X_2O]$ (M) | Acid of the Anhydride [HX'] (M) | Acid (HX) Conversion (mol %) | Anhydride $(X_2'O)$ Conversion (mol %) |
|---|---|---|---|---|
| 39 | 0.03 | N/D | 0.5% | N/D |
| 40 | 0.23 | N/D | 3.5% | N/D |
| 41 | 0.21 | N/D | 1.5% | N/D |
| 42 | 0.03 | 0.35 | 0.6% | 6.9% |
| 43 | 0.02 | 0.69 | 0.3% | 14.4% |
| 44 | 0.19 | N/D | 2.8% | N/D |
| 45 | 0.39 | N/D | 3.0% | N/D |
| 46 | 0.06 | 0.15 | 1.5% | 7.0% |
| 47 | 0.03 | 0.29 | 0.5% | 5.8% |
| 48 | 0.02 | 0.66 | 0.3% | 13.6% |
| 49 | 0.25 | N/D | 3.8% | N/D |
| 50 | 0.17 | 0.24 | 4.0% | 11.1% |
| 51 | 0.16 | 0.39 | 7.4% | 17.9% |
| 52 | 0.10 | 0.25 | 7.2% | 17.1% |
| 53 | 0.05 | N/D | 5.1% | N/D |
| 54 | 0.13 | 0.22 | 12.4% | 20.7% |
| 55 | 0.05 | 0.09 | 3.8% | 12.5% |
| 56 | 0.14 | 0.22 | 4.3% | 13.8% |
| 57 | 0.04 | 0.15 | 3.4% | 14.5% |
| 58 | 0.02 | 0.09 | 2.8% | 13.5% |
| 59 | 0.08 | 0.20 | 7.1% | 19.3% |
| 60 | 0.05 | 0.15 | 3.5% | 21.0% |
| 61 | 0.06 | 0.27 | 2.0% | 17.2% |
| 62 | 0.04 | 0.21 | 3.4% | 20.3% |
| 63 | 0.01 | 0.16 | 1.5% | 25.2% |

N/D: not determined

Example 4

This example demonstrates adding the organic mono-acid to the regenerable anhydride in stages in an embodiment of the invention.

To test the potential for multistage reactions, glutaric anhydride (10 g) was heated in a 50-ml round-bottom flask to 100° C. Acetic acid (5.25 g) was added, and the flask was sealed. After 1 hr, vacuum (10 torr (1.3 kPa)) was applied for 15 min to most of the acetic acid and acetic anhydride, the system was repressurized to atmospheric pressure, and acetic acid was added again for another cycle. The results of the cycling experiment are shown in Table 4 and demonstrate that changing the local concentrations of the material (e.g., in a reactive distillation) results in higher yields than the equilibrium would allow in a single-stage batch process.

TABLE 4

| Cycle | Glutaric Anhydride Conversion (mol %) |
|---|---|
| 1 | 5.8 |
| 2 | 10.1 |
| 3 | 14.0 |
| 4 | 17.2 |
| 5 | 20.0 |
| 6 | 23.1 |

Example 5

This example demonstrates a method of using a thermally regenerable anhydride and an organic mono-acid to generate an anhydride using a plug flow reactor (PFR) system coupled with flash distillation in an embodiment of the invention.

A 2.2:1 (by mass) solution of acetic acid and glutaric anhydride was fed under pressure into a 1 m long continuous PFR. The reactor outlet was controlled via a needle valve to maintain a consistent pressure in the reactor. A flash distillation was coupled to the PFR, by having a flash pot under vacuum after the needle valve. This allowed for separation into two streams: an acetics-rich overhead stream and a glutarics-rich bottom stream. The process conditions and results are shown in Table 5. Compositions were determined by mass and gas chromatography.

TABLE 5

| | Experiment Number | | | | | |
|---|---|---|---|---|---|---|
| | 1 | 2 | 3 | 4 | 5 | 6 |
| Flow Rate, mL/min | 7 | 7 | 7 | 7 | 7 | 25 |
| Reactor Temperature, ° C. | 150 | 181 | 210 | 140 | 140 | 140 |
| Reactor Pressure, psi (kPa) | 120 (827) | 135 (931) | 170 (1172) | 120 (827) | 120 (827) | 130 (896) |
| Flash Temperature, ° C. | 96 | 102 | 110 | 76 | 85 | 77 |
| Flash Vacuum, mm Hg (kPa) | 230 (30.7) | 230 (30.7) | 230 (30.7) | 100 (13.3) | 150 (20.0) | 100 (13.3) |
| Split to Bottom Stream, wt % | 75 | 58 | 61 | 66 | 74 | 70 |
| ACAN in Overhead Stream, wt % | 6.0 | 6.5 | 8.1 | 5.8 | 5.6 | 5.7 |
| Total ACAN Generated, wt % | 4.4 | 3.8 | 4.7 | 4.6 | 4.1 | 4.7 |

ACAN: acetic anhydride

Example 6

This example demonstrates the regeneration of a thermally regenerable anhydride for use in the transanhydridization reaction in an embodiment of the invention.

Mixtures of glutaric anhydride and glutaric acid were distilled continuously in a 3.3 m×2.5 cm Vigreux distillation column. The reboiler of the column, a 1-L round bottom flask containing approx. 350 g of material during operation, was operated as a near-total reboiler at approximately 216-231° C., with occasional sampling. The overhead condenser, a partial condenser, had a temperature between 59° C. and 78° C. The vapor distillate was condensed in a jacketed cold trap operated at approximately 5° C. The column was operated under vacuum with a head pressure between 30 mmHg and 70 mmHg (4.0 kPa and 9.3 kPa) at a liquid mass reflux ratio of 1. The feed was preheated to between 150-160° C. to ensure that the feed was in a molten state when fed to the column approximately 2.5 m from the top. Table 6 shows the average values of five or more runs at the specified conditions, with a minimum of 8 hours on stream. Compositions were determined by gas chromatography and masses were determined by weigh scales.

TABLE 6

| | Experiment Number | | | | | | |
|---|---|---|---|---|---|---|---|
| | 1 | 2 | 3 | 4 | 5 | 6 | 7 |
| Head Pressure, mmHg (kPa) | 70 (9.3) | 70 (9.3) | 70 (9.3) | 50 (6.7) | 55 (7.3) | 45 (6.0) | 30 (4.0) |
| Glutaric Acid in Feed, wt % | 15.0 | 15.0 | 30.0 | 15.0 | 30.0 | 60.0 | 59.5 |
| Feed Rate, g/hr | 248 | 373 | 248 | 248 | 248 | 250 | 251 |
| Vapor Distillate Rate, g/hr | 5 | 7 | 9 | 5 | 9 | 20 | 19 |
| Liquid Distillate Rate, g/hr | 242 | 358 | 236 | 232 | 232 | 221 | 231 |
| Vapor Water Rate, g/hr | 4 | 7 | 9 | 5 | 8 | 18 | 17 |
| Vapor Distillate Glutaric Acid, wt % | 0.1 | <0.1 | <0.1 | <0.1 | 2.2 | 4.9 | 10.9 |
| Liquid Distillate Glutaric Acid, wt % | 0.8 | 0.9 | 1.0 | <0.1 | 0.6 | 3.7 | 1.1 |
| Reboiler Glutaric Anhydride, wt % | 18.8 | 21.2 | 15.2 | 18.1 | 11.5 | 7.2 | 7.8 |
| Feed Preheat Temperature, ° C. | 160 | 160 | 160 | 150 | 155 | 150 | 150 |
| Partial Condenser Temperature, ° C. | 78 | 75 | 75 | 75 | 76 | 76 | 59 |
| Top of Column Temperature, ° C. | 202 | 202 | 201 | 192 | 194 | 186 | 175 |
| Reboiler Temperature, ° C. | 227 | 228 | 231 | 220 | 228 | 225 | 216 |

Example 7

This example demonstrates a method of producing an anhydride using a regenerable anhydride and an organic mono-acid by reactive distillation in an embodiment of the invention.

A continuous reactive distillation column packed with PRO-PAK™ structured packing (Cannon Instrument Company, State College, PA) was used to generate acetic anhydride from acetic acid and glutaric anhydride. The column was 2.5 cm in diameter and had 3.5 m of packing. An acetic acid feed entered the column approximately 3 m below the top of the packing and a glutaric anhydride feed entered the column approximately 0.5 m below the top of the column. A side draw was optionally taken from the column approximately 10 cm above the glutaric anhydride feed. The column had a total condenser operating at approximately 110° C. and a kettle reboiler, a 1-L round bottom flask, operating at a temperature of approximately 200° C. The feed and process conditions and results for the reactive distillation are shown in Table 7. Compositions were determined by gas chromatography and masses were determined by weigh scales.

TABLE 7

| | Experiment Number | | | | | | | |
|---|---|---|---|---|---|---|---|---|
| | 1 | 2 | 3 | 4 | 5 | 6 | 7 | 8 |
| Glut Anhydride Feed Rate, g/hr | 350 | 235 | 342 | 342 | 342 | 445 | 445 | 239 |
| Acetic Acid Feed Rate, g/hr | 235 | 161 | 235 | 235 | 235 | 165 | 305 | 165 |
| Distillate Reflux Ratio | 0.75 | 0.75 | 1.43 | 1.43 | 1.43 | 1.25 | 1.25 | 1.25 |
| Distillate Rate, g/hr | 202 | 139 | 113 | 114 | 118 | 75 | 159 | 75 |
| Distillate Acetic Anhydride, wt % | 10.0 | 10.4 | 0.0 | 0.0 | 0.0 | 0.0 | 0.0 | 0.0 |
| Side Stream Reflux Ratio | — | — | 3.02 | 3.02 | 3.02 | 3.20 | 3.20 | 3.20 |
| Side Stream Rate, g/hr | — | — | 59 | 64 | 65 | 48 | 63 | 49 |
| Side Stream Acetic Anhydride, wt % | — | — | 17.1 | 16.2 | 19.3 | 22.8 | 20.9 | 16.9 |
| Bottom Rate, g/hr | 383 | 257 | 405 | 400 | 395 | 488 | 511 | 280 |
| Bottom Acetic Acid, wt % | 7.8 | 7.7 | 7.6 | 7.7 | 7.9 | 7.5 | 7.9 | 7.2 |
| Bottom Acetic Anhydride, wt % | 0.9 | 0.9 | 0.0 | 0.0 | 0.0 | 0.0 | 0.0 | 0.0 |
| Bottom Glutaric Acid, wt % | 7.9 | 7.6 | 2.8 | 2.9 | 3.6 | 2.5 | 3.6 | 3.3 |
| Pressure, mmHg (kPa) | 760 (101) | 760 (101) | 760 (101) | 760 (101) | 760 (101) | 760 (101) | 760 (101) | 760 (101) |
| Glutaric Anhydride Feed Temperature, ° C. | 100 | 100 | 135 | 154 | 175 | 175 | 175 | 175 |
| Acetic Acid Feed Temperature, ° C. | 100 | 95 | 100 | 100 | 100 | 100 | 100 | 100 |
| Head Temperature, ° C. | 120 | 119 | 116 | 115 | 116 | 114 | 117 | 113 |
| Side Stream Temperature, ° C. | — | — | 119 | 119 | 119 | 119 | 120 | 117 |
| Kettle Temperature, ° C. | 203 | 200 | 200 | 200 | 200 | 200 | 200 | 200 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B")

is to be construed to mean one item selected from the listed items (A or B) or any combination of two or more of the listed items (A and B), unless otherwise indicated herein or clearly contradicted by context. The terms “comprising,” “having,” “including,” and “containing” are to be construed as open-ended terms (i.e., meaning “including, but not limited to,”) unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., “such as”) provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A first process of producing acetic anhydride comprising performing a preprocess that uses acetic anhydride as a reactant, wherein the preprocess is an acetylated wood process comprising reacting acetic anhydride with a feedstock to produce a desired product and an acetic acid by-product stream;

separating the desired product and acetic acid by-product stream, wherein the acetic acid by-product stream further comprises at least one terpene;

feeding the acetic acid by-product stream comprising at least one terpene into a transanhydridization reaction; and performing a transanhydridization reaction of acetic acid and glutaric anhydride to produce acetic anhydride and glutaric acid in the presence of at least one terpene, wherein the transanhydridization reaction excludes the use of perchloric acid.

2. The process of claim 1, comprising separating the acetic anhydride and the glutaric acid;

recycling the acetic anhydride to the preprocess;

heating the glutaric acid to produce glutaric anhydride; and recycling the regenerated glutaric anhydride for the transanhydridization.

3. The process of claim 1, comprising separating the acetic anhydride and the glutaric acid;

recycling the acetic anhydride to the preprocess as a reagent;

heating the glutaric acid to produce regenerated glutaric anhydride; and recycling the regenerated glutaric anhydride for the transanhydridization.

4. A process comprising a wood acetylation process coupled to an acetic anhydride production process, wherein the wood acetylation process comprises subjecting wood to acetylation with an acetylation fluid to produce an acetylated wood product and an acetic acid by-product stream comprising at least one terpene, and the acetic anhydride production process comprises performing a transanhydridization reaction between acetic acid and a glutaric anhydride to produce an acetic anhydride reaction fluid comprising acetic anhydride and acetic acid, wherein the anhydride reaction fluid is used in the wood acetylation process as an acetylation fluid, wherein the transanhydridization reaction excludes the use of perchloric acid.

5. An integrated wood acetylation and anhydride production system comprising a wood acetylation vessel for receiving wood and an acetylation fluid that is in fluid communication with a first fluid channel for conveying recovered acetylation fluid;

a first separation vessel for receiving the recovered acetylation fluid from the first fluid channel and that is in fluid communication with a recovered acetic anhydride vessel and an acetic acid by-product vessel;

a transanhydridization vessel for receiving acetic acid by-product and glutaric anhydride that is in fluid communication with (a) the acetic acid by-product vessel; and (b) a second fluid channel for conveying the glutaric anhydride;

a third fluid channel for conveying acetic anhydride and glutaric acid to a second separation vessel;

a fourth fluid channel for conveying separated acetic anhydride from the second separation vessel to a first anhydride vessel;

a fifth fluid channel for conveying separated glutaric acid from the second separation vessel to a regeneration vessel;

wherein the first anhydride vessel is in fluid communication with the wood acetylation vessel; and the regeneration vessel is in fluid communication with the second fluid channel, wherein the transanhydridization vessel contains a transanhydrization reaction, wherein the transanhydridization reaction excludes the use of perchloric acid.

6. A process of supplying an acetic acid reactant feed to a transanhydridization reaction unit, comprising supplying an acetic acid reactant feed to a transanhydridization reaction unit, wherein the acetic acid reactant feed is acetylation fluid that has been directly recovered from a wood acetylation process and which comprises at least one terpene, acetic acid and acetic anhydride, and wherein the wood acetylation process comprises reacting acetic anhydride with a feedstock to produce an acetylated wood product and an acetic acid by-product stream comprising at least one terpene, wherein the transanhydridization reaction unit contains a transanhydrization reaction, wherein the transanhydridization reaction excludes the use of perchloric acid.

7. The process of claim 1, wherein the acetic acid reactant feed comprises at least 20 ppm of terpenes.

8. The process of claim 1, wherein the acetic acid reactant feed comprises at least 100 ppm of terpenes.

9. The process of claim 1, wherein the acetic acid reactant feed comprises at least 1,000 ppm of terpenes.

10. The process of claim 1, wherein the acetic acid reactant feed comprises 6,000 ppm or less of terpenes.

* * * * *